(12) United States Patent
Halazonetis

(10) Patent No.: US 7,303,866 B2
(45) Date of Patent: Dec. 4, 2007

(54) METHODS OF IDENTIFYING AN AGENT THAT MODULATES AN INTERACTION BETWEEN 53BP1 AND HISTONE H3, AND USES THEREOF

(75) Inventor: Thanos D. Halazonetis, 765 Periwinkle La., Wynnewood, PA (US) 19096

(73) Assignee: Thanos D. Halazonetis, Geneva (CH)

( * ) Notice: Subject to any disclaimer, the term of this patent is extended or adjusted under 35 U.S.C. 154(b) by 87 days.

(21) Appl. No.: 11/253,190

(22) Filed: Oct. 17, 2005

(65) Prior Publication Data

US 2006/0115839 A1 Jun. 1, 2006

Related U.S. Application Data

(60) Provisional application No. 60/620,461, filed on Oct. 19, 2004.

(51) Int. Cl.
*C12Q 1/00* (2006.01)
(52) U.S. Cl. .......................................................... 435/4
(58) Field of Classification Search ..................... None
See application file for complete search history.

(56) References Cited

OTHER PUBLICATIONS

Bowie et al (Science, 1990, 257:1306-1310).*
Lazar et al (Molecular and Cellular Biology, 1988, 8:1247-1252).*
Burgess et al (J of Cell Bio. 111:2129-2138, 1990).*
Anderson et al., "Phosphorylation and rapid relocalization of 53BP1 to nuclear foci upon DNA damage," *Molecular and Cellular Biology* (2001) 21(5):1719-1729.
Bakkenist et al., "DNA damage activates ATM through intermolecular autophosphorylation and dimer dissociation," *Nature* (2003) 421(6922):499-506.
Bergendahl et al., "Luminescence resonance energy transfer-based high-throughput screening assay for inhibitors of essential protein-protein interactions in bacterial RNA polymerase," *Appl Environ Microbiol.* (2003) 69(3):1492-1498.
Boulton et al., "Combined functional genomic maps of the *C. elegans* DNA damage response," *Science* (2002) 295(5552):127-131.
Boute et al., "The use of resonance energy transfer in high-throughput screening: BRET versus FRET," *Trends Pharmacol Sci.* (2002) 23(8):351-354.
Brahms et al., "Symmetrical dimethylation of arginine residues in spliceosomal Sm protein B/B" and the Sm-like protein LSm4 and their interaction with the SMN protein," *RNA* (2001) 7:1531-1542.
Celeste et al., "Histone H2AX phosphorylation is dispensable for the initial recognition of DNA breaks," *Nature Cell Biology* (2003) 5(7):675-679.
Charier et al., "The Tudor tandem of 53BPI: a new structural motif involved in DNA and RG-rich peptide binding," *Structure* (2004) 12(9):1551-1562.
Cunningham et al., "Label-free assays on the BIND system," *J. Biomol Screen* (2004) 9(6):481-490.
Feng et al., "Methylation of H3-Lysine 79 Is Mediated by a New Family of HMTases without a SET Domain," *Current Biology* (2002) 12(12)1052-1058.
Friesen et al., "SMN, the product of the spinal muscular atrophy gene, binds preferentially to dimethylarginine-containing protein targets," *Molecular Cell* (2001) 7(5):1111-1117.
Gadek "Strategies and methods in the identification of antagonists of protein-protein interactions," *Biotechniques* (2003) Suppl:21-24.
Gadek et al., "Small molecule antagonists of proteins," *Biochem Pharmacol* (2003) 65(1):1-8.
Game et al., "X-ray survival characteristics and genetic analysis for nine Saccharomyces deletion mutants that show altered radiation sensitivity," *Genetics* (2005) 169(1):51-63.
Huyen et al., "Structural differences in the DNA binding domains of human p53 and its *C. elegans* ortholog Cep-1," *Structure* (2004) 12(7):1237-1243.
Iwabuchi et al., "Potential role for 53BP1 in the DNA end-joining repair through direct interaction with DNA," *The Journal of Biological Chemistry* (2003) 278(38):36487-36495.
Kannouche et al., "Interaction of human DNA polymerase eta with monoubiquitinated PCNA: a possible mechanism for the polymerase switch in response to DNA damage," *Molecular Cell* (2004) 14(4):491-500.
Kay et al., "High-throughput screening strategies to identify inhibitors of protein-protein interactions," *Mol. Divers.* (1996) 1(2):139-140.
Kouzarides, "Histone methylation in transcriptional control," *Current Opinion in Genetics and Development* (2002) 12(2)198-209.
Lacoste et al., "Disruptor of telomeric silencing-1 is a chromatin-specific histone H3 methyltransferase," *The Journal of Biological Chemistry* (2002) 277(34):30421-30424.
Luger et al., "Crystal structure of the nucleosome core particle at 2.8 A resolution," *Nature* (1997) 389(6648):251-260.
Mochan et al., "53BP1 and NFBD1/MDC1-Nbs1 function in parallel interacting pathways activating ataxia-telangiectasia mutated (ATM) in response to DNA damage," *Cancer Research* (2003) 63(24):8586-8591.
Mozziconacci et al., "Nucleosome gaping supports a functional structure for the 30nm chromatin fiber," *Journal of Structural Biology* (2003) 143(1):72-76.
Pierceall et al., "Affinity capillary electrophoresis analyses of protein-protein interactions in target-directed drug discovery," *Methods Mol. Biol.* (2004) 261:187-198.
Rappold et al., "Tumor suppressor p53 binding protein 1 (53BP1) is involved in DNA damage-signaling pathways," *The Journal of Cell Biology* (2001) 153(3):613-620.
Rogakou et al., "Megabase chromatin domains involved in DNA double-strand breaks in vivo," *J Cell Biol* (1999) 146(5):905-916.
Saka et al., "Damage and replication checkpoint control in fission yeast is ensured by interactions of Crb2, a protein with BRCT motif, with Cut5 and Chk1," *Genes & Development* (1997) 11(24):3387-3400.
San-Segundo et al., "Role for the silencing protein Dot1 in meiotic checkpoint control," *Mol Biol Cell* (2000) 11(10):3601-3615.

(Continued)

*Primary Examiner*—Karen A. Canella
*Assistant Examiner*—Catherine Joyce
(74) *Attorney, Agent, or Firm*—Pepper Hamilton LLP

(57) ABSTRACT

The present invention relates to methods of identifying modulators of an interaction between 53BP1 and histone H3 (H3). The present invention also relates to methods of use of inhibitors of an interaction between 53BP1 and H3. The present invention further relates to fragments of 53BP1 and H3, as well as other methods and uses.

7 Claims, 5 Drawing Sheets

OTHER PUBLICATIONS

Schultz et al., "p53 binding protein 1 (53BP1) is an early participant in the cellular response to DNA double-strand breaks," *The Journal of Cell Biology* (2000) 151(7):1381-1390.

Selenko et al., "SMN tudor domain structure and its interaction with the Sm proteins," *Nat Struct Biol* (2001) 8(1):27-31.

Sprangers et al., "High-resolution X-ray and NMR structures of the SMN Tudor domain: conformational variation in the binding site for symmetrically dimethylated arginine residues," *J Mol Biol* (2003) 327(2):507-520.

Theobald et al., "Nucleic acid recognition by OB-fold proteins," *Annu Rev Biophys Biomol Struct* (2003) 32:115-133.

Van Leeuwen et al., "Dot1p modulates silencing in yeast by methylation of the nucleosome core," *Cell* (2002) 109(6):745-756.

Ward et al., "Accumulation of checkpoint protein 53BP1 at DNA breaks involves its binding to phosphorylated histone H2AX," *The Journal of Biological Chemistry* (2003) 278(22):19579-19582.

Weinert et al., "The RAD9 gene controls the cell cycle response to DNA damage in *Saccharomyces cerevisiae*," *Science* (1988) 241(4863):317-322.

Willson et al., "Isolation and characterization of the *Schizosaccharomyces pombe* rhp9 gene: a gene required for the DNA damage checkpoint but not the replication checkpoint," *Nucleic Acids Research* (1997) 25(11):2138-2146.

Xia et al., "Negative cell cycle regulation and DNA damage-inducible phosphorylation of the BRCT protein 53BP1," *The Journal of Biological Chemistry* (2001) 276(4):2708-2718.

Huyen et al., "Methylated lysine 79 of histone H3 targets 53BP1 to DNA double-strand breaks," *Nature* (2004) 432(7015):406-411.

Ward et al., "53BP1 is required for class switch recombination," *J Cell Biol* (2004) 165(4):459-464.

\* cited by examiner

Figure 1

```
               1         1         1         1
       149     150       152       153
       6789012345678.90123456...789012.3..4567890.12345678
                  ==s1=>      =====s2=====>    ==s3==>     ==s4=>  s5>
53BP1hs 1486 FVGLRVVAKWSSN.GYFYSGKI..TRDVGA.G..KYKLLFD.DGYECDVLGKDILLCDPI 1538
53BP1xl 1689 FMGLRVVAKWSSN.GYFYSGKI..TQDAGG.G..KYKLLFD.DGYECDVLGKDILLCDPI 1741
HSR9ce   734 APGARVYAVFQK...MFYPAVV..LSERDGLG..RYKVQFTVDNVIKDVPNSGIIPLRAL  786
RAD9sc   782 IFGNAVWCQYTWN.YKFYPGILL.EVDTNQDG...CWIYFE.TGRS.LTKDEDIYYLDIR  834
RHP9sp   361 SFKNRVLAFFKGYPSFYYPATLVAPVHSAVTSSIMYKVQFD.DATMSTVNSNQIKRFFLK  419

1                    1
               15                   16
               4                    0
       .9012345678901234567.890123456789012345.........6789012345678901234567890
            ==s6=>       ==== ==s7====>    ===s8===>                   ==s9==>   s10<===h1===>
53BP1hs 1539 .PLDTEVTALSEDEYFSAGV.VKGHRKESGELYYSIEKE.........GQRKWYKRMAVILSLEQGNRLREQYGL 1602
53BP1xl 1742 .PLDSEVTALSDDEYFSAGV.VKAHKKDSEELYYCIEKD.........GQRKWYKRMAVILSLEQGNRLREQYGL 1805
HSR9ce   787 SPGKTAVYNESDVRLDSGPNDISAAEWKKGKLTISIMDE........DGEPTDEVKVVDWYDVSFD.HSEWRDYVKS 854
RAD9sc   835 ..IGDAVTFDG.NEYVVVGLECRSHDL..NIIRCIRGYDTVHLKKKNASGLLGKRTLIKALSSISLD.LSEWAKRAKI 906
RHP9sp   420 ..KGDVVQSTRLGKIKHTV..VKTFRSTNEQLSLIAVDA.....LNNDMVILAHGEIEVTVPISTIYVAPVNIRRFQ  487
``` ers. This application claims priority to U.S. provisional application 60/620,461, filed Oct. 19, 2004, which is hereby incorporated by reference in its entirety.

SEQUENCE LISTING

```
<160> NUMBER OF SEQ ID NOS: 4

<210> SEQ ID NO 1
<211> LENGTH: 1972
<212> TYPE: PRT
<213> ORGANISM: Homo sapiens

<400> SEQUENCE: 1

Met Asp Pro Thr Gly Ser Gln Leu Asp Ser Asp Phe Ser Gln Gln Asp
1               5                   10                  15

Thr Pro Cys Leu Ile Ile Glu Asp Ser Gln Pro Glu Ser Gln Val Leu
            20                  25                  30
```

```
Glu Asp Asp Ser Gly Ser His Phe Ser Met Leu Ser Arg His Leu Pro
        35                  40                  45
Asn Leu Gln Thr His Lys Glu Asn Pro Val Leu Asp Val Val Ser Asn
    50                  55                  60
Pro Glu Gln Thr Ala Gly Glu Arg Gly Asp Gly Asn Ser Gly Phe
65                  70                  75                  80
Asn Glu His Leu Lys Glu Asn Lys Val Ala Asp Pro Val Asp Ser Ser
                85                  90                  95
Asn Leu Asp Thr Cys Gly Ser Ile Ser Gln Val Ile Glu Gln Leu Pro
            100                 105                 110
Gln Pro Asn Arg Thr Ser Ser Val Leu Gly Met Ser Val Glu Ser Ala
            115                 120                 125
Pro Ala Val Glu Glu Glu Lys Gly Glu Glu Leu Glu Gln Lys Glu Lys
130                 135                 140
Glu Lys Glu Glu Asp Thr Ser Gly Asn Thr Thr His Ser Leu Gly Ala
145                 150                 155                 160
Glu Asp Thr Ala Ser Ser Gln Leu Gly Phe Gly Val Leu Glu Leu Ser
                165                 170                 175
Gln Ser Gln Asp Val Glu Glu Asn Thr Val Pro Tyr Glu Val Asp Lys
            180                 185                 190
Glu Gln Leu Gln Ser Val Thr Thr Asn Ser Gly Tyr Thr Arg Leu Ser
            195                 200                 205
Asp Val Asp Ala Asn Thr Ala Ile Lys His Glu Glu Gln Ser Asn Glu
            210                 215                 220
Asp Ile Pro Ile Ala Glu Gln Ser Ser Lys Asp Ile Pro Val Thr Ala
225                 230                 235                 240
Gln Pro Ser Lys Asp Val His Val Val Lys Glu Gln Asn Pro Pro
            245                 250                 255
Ala Arg Ser Glu Asp Met Pro Phe Ser Pro Lys Ala Ser Val Ala Ala
            260                 265                 270
Met Glu Ala Lys Glu Gln Leu Ser Ala Gln Glu Leu Met Glu Ser Gly
        275                 280                 285
Leu Gln Ile Gln Lys Ser Pro Glu Pro Glu Val Leu Ser Thr Gln Glu
        290                 295                 300
Asp Leu Phe Asp Gln Ser Asn Lys Thr Val Ser Ser Asp Gly Cys Ser
305                 310                 315                 320
Thr Pro Ser Arg Glu Glu Gly Gly Cys Ser Leu Ala Ser Thr Pro Ala
            325                 330                 335
Thr Thr Leu His Leu Leu Gln Leu Ser Gly Gln Arg Ser Leu Val Gln
            340                 345                 350
Asp Ser Leu Ser Thr Asn Ser Ser Asp Leu Val Ala Pro Ser Pro Asp
            355                 360                 365
Ala Phe Arg Ser Thr Pro Phe Ile Val Pro Ser Ser Pro Thr Glu Gln
            370                 375                 380
Glu Gly Arg Gln Asp Lys Pro Met Asp Thr Ser Val Leu Ser Glu Glu
385                 390                 395                 400
Gly Gly Glu Pro Phe Gln Lys Lys Leu Gln Ser Gly Glu Pro Val Glu
                405                 410                 415
Leu Glu Asn Pro Pro Leu Leu Pro Glu Ser Thr Val Ser Pro Gln Ala
            420                 425                 430
Ser Thr Pro Ile Ser Gln Ser Thr Pro Val Phe Pro Pro Gly Ser Leu
            435                 440                 445
Pro Ile Pro Ser Gln Pro Gln Phe Ser His Asp Ile Phe Ile Pro Ser
```

-continued

```
            450                 455                 460
Pro Ser Leu Glu Glu Gln Ser Asn Asp Gly Lys Asp Gly Asp Met
465                 470                 475                 480

His Ser Ser Ser Leu Thr Val Glu Cys Ser Lys Thr Ser Glu Ile Glu
                485                 490                 495

Pro Lys Asn Ser Pro Glu Asp Leu Gly Leu Ser Leu Thr Gly Asp Ser
                500                 505                 510

Cys Lys Leu Met Leu Ser Thr Ser Glu Tyr Ser Gln Ser Pro Lys Met
                515                 520                 525

Glu Ser Leu Ser Ser His Arg Ile Asp Glu Asp Gly Glu Asn Thr Gln
            530                 535                 540

Ile Glu Asp Thr Glu Pro Met Ser Pro Val Leu Asn Ser Lys Phe Val
545                 550                 555                 560

Pro Ala Glu Asn Asp Ser Ile Leu Met Asn Pro Ala Gln Asp Gly Glu
                565                 570                 575

Val Gln Leu Ser Gln Asn Asp Asp Lys Thr Lys Gly Asp Asp Thr Asp
                580                 585                 590

Thr Arg Asp Asp Ile Ser Ile Leu Ala Thr Gly Cys Lys Gly Arg Glu
            595                 600                 605

Glu Thr Val Ala Glu Asp Val Cys Ile Asp Leu Thr Cys Asp Ser Gly
            610                 615                 620

Ser Gln Ala Val Pro Ser Pro Ala Thr Arg Ser Glu Ala Leu Ser Ser
625                 630                 635                 640

Val Leu Asp Gln Glu Glu Ala Met Glu Ile Lys Glu His His Pro Glu
                645                 650                 655

Glu Gly Ser Ser Gly Ser Glu Val Glu Glu Ile Pro Glu Thr Pro Cys
            660                 665                 670

Glu Ser Gln Gly Glu Glu Leu Lys Glu Glu Asn Met Glu Ser Val Pro
            675                 680                 685

Leu His Leu Ser Leu Thr Glu Thr Gln Ser Gln Gly Leu Cys Leu Gln
            690                 695                 700

Lys Glu Met Pro Lys Lys Glu Cys Ser Glu Ala Met Glu Val Glu Thr
705                 710                 715                 720

Ser Val Ile Ser Ile Asp Ser Pro Gln Lys Leu Ala Ile Leu Asp Gln
                725                 730                 735

Glu Leu Glu His Lys Glu Gln Glu Ala Trp Glu Glu Ala Thr Ser Glu
                740                 745                 750

Asp Ser Ser Val Val Ile Val Asp Val Lys Glu Pro Ser Pro Arg Val
            755                 760                 765

Asp Val Ser Cys Glu Pro Leu Glu Gly Val Glu Lys Cys Ser Asp Ser
            770                 775                 780

Gln Ser Trp Glu Asp Ile Ala Pro Glu Ile Glu Pro Cys Ala Glu Asn
785                 790                 795                 800

Arg Leu Asp Thr Lys Glu Glu Lys Ser Val Glu Tyr Glu Gly Asp Leu
                805                 810                 815

Lys Ser Gly Thr Ala Glu Thr Glu Pro Val Glu Gln Asp Ser Ser Gln
                820                 825                 830

Pro Ser Leu Pro Leu Val Arg Ala Asp Asp Pro Leu Arg Leu Asp Gln
                835                 840                 845

Glu Leu Gln Gln Pro Gln Thr Gln Glu Lys Thr Ser Asn Ser Leu Thr
            850                 855                 860

Glu Asp Ser Lys Met Ala Asn Ala Lys Gln Leu Ser Ser Asp Ala Glu
865                 870                 875                 880
```

-continued

```
Ala Gln Lys Leu Gly Lys Pro Ser Ala His Ala Ser Gln Ser Phe Cys
            885                 890                 895
Glu Ser Ser Ser Glu Thr Pro Phe His Phe Thr Leu Pro Lys Glu Gly
            900                 905                 910
Asp Ile Ile Pro Pro Leu Thr Gly Ala Thr Pro Pro Leu Ile Gly His
            915                 920                 925
Leu Lys Leu Glu Pro Lys Arg His Ser Thr Pro Ile Gly Ile Ser Asn
            930                 935                 940
Tyr Pro Glu Ser Thr Ile Ala Thr Ser Asp Val Met Ser Glu Ser Met
945                 950                 955                 960
Val Glu Thr His Asp Pro Ile Leu Gly Ser Gly Lys Gly Asp Ser Gly
            965                 970                 975
Ala Ala Pro Asp Val Asp Asp Lys Leu Cys Leu Arg Met Lys Leu Val
            980                 985                 990
Ser Pro Glu Thr Glu Ala Ser Glu Glu Ser Leu Gln Phe Asn Leu Glu
            995                1000                1005
Lys Pro Ala Thr Gly Glu Arg Lys Asn Gly Ser Thr Ala Val Ala
            1010               1015                1020
Glu Ser Val Ala Ser Pro Gln Lys Thr Met Ser Val Leu Ser Cys
            1025               1030                1035
Ile Cys Glu Ala Arg Gln Glu Asn Glu Ala Arg Ser Glu Asp Pro
            1040               1045                1050
Pro Thr Thr Pro Ile Arg Gly Asn Leu Leu His Phe Pro Ser Ser
            1055               1060                1065
Gln Gly Glu Glu Glu Lys Glu Lys Leu Glu Gly Asp His Thr Ile
            1070               1075                1080
Arg Gln Ser Gln Gln Pro Met Lys Pro Ile Ser Pro Val Lys Asp
            1085               1090                1095
Pro Val Ser Pro Ala Ser Gln Lys Met Val Ile Gln Gly Pro Ser
            1100               1105                1110
Ser Pro Gln Gly Glu Ala Met Val Thr Asp Val Leu Glu Asp Gln
            1115               1120                1125
Lys Glu Gly Arg Ser Thr Asn Lys Glu Asn Pro Ser Lys Ala Leu
            1130               1135                1140
Ile Glu Arg Pro Ser Gln Asn Asn Ile Gly Ile Gln Thr Met Glu
            1145               1150                1155
Cys Ser Leu Arg Val Pro Glu Thr Val Ser Ala Ala Thr Gln Thr
            1160               1165                1170
Ile Lys Asn Val Cys Glu Gln Gly Thr Ser Thr Val Asp Gln Asn
            1175               1180                1185
Phe Gly Lys Gln Asp Ala Thr Val Gln Thr Glu Arg Gly Ser Gly
            1190               1195                1200
Glu Lys Pro Val Ser Ala Pro Gly Asp Asp Thr Glu Ser Leu His
            1205               1210                1215
Ser Gln Gly Glu Glu Glu Phe Asp Met Pro Gln Pro Pro His Gly
            1220               1225                1230
His Val Leu His Arg His Met Arg Thr Ile Arg Glu Val Arg Thr
            1235               1240                1245
Leu Val Thr Arg Val Ile Thr Asp Val Tyr Tyr Val Asp Gly Thr
            1250               1255                1260
Glu Val Glu Arg Lys Val Thr Glu Glu Thr Glu Glu Pro Ile Val
            1265               1270                1275
```

-continued

```
Glu Cys Gln Glu Cys Glu Thr Glu Val Ser Pro Ser Gln Thr Gly
1280                1285                1290

Gly Ser Ser Gly Asp Leu Gly Asp Ile Ser Ser Phe Ser Ser Lys
    1295                1300                1305

Ala Ser Ser Leu His Arg Thr Ser Ser Gly Thr Ser Leu Ser Ala
1310                1315                1320

Met His Ser Ser Gly Ser Ser Gly Lys Gly Ala Gly Pro Leu Arg
1325                1330                1335

Gly Lys Thr Ser Gly Thr Glu Pro Ala Asp Phe Ala Leu Pro Ser
1340                1345                1350

Ser Arg Gly Gly Pro Gly Lys Leu Ser Pro Arg Lys Gly Val Ser
1355                1360                1365

Gln Thr Gly Thr Pro Val Cys Glu Glu Asp Gly Asp Ala Gly Leu
1370                1375                1380

Gly Ile Arg Gln Gly Gly Lys Ala Pro Val Thr Pro Arg Gly Arg
1385                1390                1395

Gly Arg Arg Gly Arg Pro Pro Ser Arg Thr Thr Gly Thr Arg Glu
1400                1405                1410

Thr Ala Val Pro Gly Pro Leu Gly Ile Glu Asp Ile Ser Pro Asn
1415                1420                1425

Leu Ser Pro Asp Asp Lys Ser Phe Ser Arg Val Val Pro Arg Val
1430                1435                1440

Pro Asp Ser Thr Arg Arg Thr Asp Val Gly Ala Gly Ala Leu Arg
1445                1450                1455

Arg Ser Asp Ser Pro Glu Ile Pro Phe Gln Ala Ala Ala Gly Pro
1460                1465                1470

Ser Asp Gly Leu Asp Ala Ser Ser Pro Gly Asn Ser Phe Val Gly
1475                1480                1485

Leu Arg Val Val Ala Lys Trp Ser Ser Asn Gly Tyr Phe Tyr Ser
1490                1495                1500

Gly Lys Ile Thr Arg Asp Val Gly Ala Gly Lys Tyr Lys Leu Leu
1505                1510                1515

Phe Asp Asp Gly Tyr Glu Cys Asp Val Leu Gly Lys Asp Ile Leu
1520                1525                1530

Leu Cys Asp Pro Ile Pro Leu Asp Thr Glu Val Thr Ala Leu Ser
1535                1540                1545

Glu Asp Glu Tyr Phe Ser Ala Gly Val Val Lys Gly His Arg Lys
1550                1555                1560

Glu Ser Gly Glu Leu Tyr Tyr Ser Ile Glu Lys Glu Gly Gln Arg
1565                1570                1575

Lys Trp Tyr Lys Arg Met Ala Val Ile Leu Ser Leu Glu Gln Gly
1580                1585                1590

Asn Arg Leu Arg Glu Gln Tyr Gly Leu Gly Pro Tyr Glu Ala Val
1595                1600                1605

Thr Pro Leu Thr Lys Ala Ala Asp Ile Ser Leu Asp Asn Leu Val
1610                1615                1620

Glu Gly Lys Arg Lys Arg Arg Ser Asn Val Ser Ser Pro Ala Thr
1625                1630                1635

Pro Thr Ala Ser Ser Ser Ser Thr Thr Pro Thr Arg Lys Ile
1640                1645                1650

Thr Glu Ser Pro Arg Ala Ser Met Gly Val Leu Ser Gly Lys Arg
1655                1660                1665

Lys Leu Ile Thr Ser Glu Glu Glu Arg Ser Pro Ala Lys Arg Gly
```

|   |   |   |   |   |   |   |   |   |   |
|---|---|---|---|---|---|---|---|---|---|
|   | 1670 |   |   | 1675 |   |   | 1680 |   |   |
| Arg | Lys | Ser | Ala | Thr | Val | Lys | Pro | Gly | Ala | Val | Gly | Ala | Gly | Glu |
|   | 1685 |   |   |   | 1690 |   |   |   | 1695 |   |
| Phe | Val | Ser | Pro | Cys | Glu | Ser | Gly | Asp | Asn | Thr | Gly | Glu | Pro | Ser |
|   | 1700 |   |   |   | 1705 |   |   |   | 1710 |   |
| Ala | Leu | Glu | Glu | Gln | Arg | Gly | Pro | Leu | Pro | Leu | Asn | Lys | Thr | Leu |
|   | 1715 |   |   |   | 1720 |   |   |   | 1725 |   |
| Phe | Leu | Gly | Tyr | Ala | Phe | Leu | Leu | Thr | Met | Ala | Thr | Thr | Ser | Asp |
|   | 1730 |   |   |   | 1735 |   |   |   | 1740 |   |
| Lys | Leu | Ala | Ser | Arg | Ser | Lys | Leu | Pro | Asp | Gly | Pro | Thr | Gly | Ser |
|   | 1745 |   |   |   | 1750 |   |   |   | 1755 |   |
| Ser | Glu | Glu | Glu | Glu | Phe | Leu | Glu | Ile | Pro | Pro | Phe | Asn | Lys |
|   | 1760 |   |   |   | 1765 |   |   |   | 1770 |   |
| Gln | Tyr | Thr | Glu | Ser | Gln | Leu | Arg | Ala | Gly | Ala | Gly | Tyr | Ile | Leu |
|   | 1775 |   |   |   | 1780 |   |   |   | 1785 |   |
| Glu | Asp | Phe | Asn | Glu | Ala | Gln | Cys | Asn | Thr | Ala | Tyr | Gln | Cys | Leu |
|   | 1790 |   |   |   | 1795 |   |   |   | 1800 |   |
| Leu | Ile | Ala | Asp | Gln | His | Cys | Arg | Thr | Arg | Lys | Tyr | Phe | Leu | Cys |
|   | 1805 |   |   |   | 1810 |   |   |   | 1815 |   |
| Leu | Ala | Ser | Gly | Ile | Pro | Cys | Val | Ser | His | Val | Trp | Val | His | Asp |
|   | 1820 |   |   |   | 1825 |   |   |   | 1830 |   |
| Ser | Cys | His | Ala | Asn | Gln | Leu | Gln | Asn | Tyr | Arg | Asn | Tyr | Leu | Leu |
|   | 1835 |   |   |   | 1840 |   |   |   | 1845 |   |
| Pro | Ala | Gly | Tyr | Ser | Leu | Glu | Glu | Gln | Arg | Ile | Leu | Asp | Trp | Gln |
|   | 1850 |   |   |   | 1855 |   |   |   | 1860 |   |
| Pro | Arg | Glu | Asn | Pro | Phe | Gln | Asn | Leu | Lys | Val | Leu | Leu | Val | Ser |
|   | 1865 |   |   |   | 1870 |   |   |   | 1875 |   |
| Asp | Gln | Gln | Gln | Asn | Phe | Leu | Glu | Leu | Trp | Ser | Glu | Ile | Leu | Met |
|   | 1880 |   |   |   | 1885 |   |   |   | 1890 |   |
| Thr | Gly | Gly | Ala | Ala | Ser | Val | Lys | Gln | His | His | Ser | Ser | Ala | His |
|   | 1895 |   |   |   | 1900 |   |   |   | 1905 |   |
| Asn | Lys | Asp | Ile | Ala | Leu | Gly | Val | Phe | Asp | Val | Val | Thr | Asp |
|   | 1910 |   |   |   | 1915 |   |   |   | 1920 |   |
| Pro | Ser | Cys | Pro | Ala | Ser | Val | Leu | Lys | Cys | Ala | Glu | Ala | Leu | Gln |
|   | 1925 |   |   |   | 1930 |   |   |   | 1935 |   |
| Leu | Pro | Val | Val | Ser | Gln | Glu | Trp | Val | Ile | Gln | Cys | Leu | Ile | Val |
|   | 1940 |   |   |   | 1945 |   |   |   | 1950 |   |
| Gly | Glu | Arg | Ile | Gly | Phe | Lys | Gln | His | Pro | Lys | Tyr | Lys | His | Asp |
|   | 1955 |   |   |   | 1960 |   |   |   | 1965 |   |
| Tyr | Val | Ser | His |
|   | 1970 |   |   |

<210> SEQ ID NO 2
<211> LENGTH: 136
<212> TYPE: PRT
<213> ORGANISM: Homo sapiens

<400> SEQUENCE: 2

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
                20                  25                  30

Thr Gly Gly Val Lys Lys Pro His Arg Tyr Arg Pro Gly Thr Val Ala
            35                  40                  45

```
Leu Arg Glu Ile Arg Arg Tyr Gln Lys Ser Thr Glu Leu Leu Ile Arg
 50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ser Ala Val Met Ala Leu Gln Glu Ala
                 85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 3
<211> LENGTH: 21
<212> TYPE: DNA
<213> ORGANISM: artificial sequence
<220> FEATURE:
<223> OTHER INFORMATION: synthetic nucleotide

<400> SEQUENCE: 3
gcucgcuaug gagaauuact t                                                    21

<210> SEQ ID NO 4
<211> LENGTH: 6266
<212> TYPE: DNA
<213> ORGANISM: Homo sapiens

<400> SEQUENCE: 4
cgttgtttgg cgtgtttttt tttttgtttt ttgtcactgc ctgcctgggt cctgcccgag          60
gtctccatcc tcggtttccc tgtccttgcc ccgggccctg ggagtgctct ggaaggctgc         120
gcagtattgg aggggacaga atgaccttcc ggccttgagt ccctggggag cagatggacc         180
ctactggaag tcagttggat tcagatttct ctcagcaaga tactccttgc ctgataattg         240
aagattctca gcctgaaagc caggttctag aggatgattc tggttctcac ttcagtatgc         300
tatctcgaca ccttcctaat ctccagacgc acaagaaaaa tcctgtgttg gatgttgtgt         360
ccaatcctga caaacagct ggagaagaac gaggagacgg taatagtggg ttcaatgaac          420
atttgaaaga aaacaaggtt gcagaccctg tggattcttc taacttggac acatgtggtt         480
ccatcagtca ggtcattgag cagttacctc agccaaacag gacaagcagt gttctgggaa         540
tgtcagtgga atctgctcct gctgtggagg aagaagggg agaagagttg aacagaaggg          600
agaaagagaa ggaagaagat acttcaggca atactacaca ttcccttggt gctgaagata         660
ctgcctcatc acagttgggt tttgggggttc tggaactctc ccagagccag gatgttgagg        720
aaaatactgt gccatatgaa gtggacaaag agcagctaca atcagtaacc accaactctg         780
gttataccag gctgtctgat gtggatgcta atactgcaat taagcatgaa gaacagtcca         840
acgaagatat ccccatagca gaacagtcca gcaaggacat ccctgtgaca gcacagccca         900
gtaaggatgt acatgttgta aaagagcaaa atccaccacc tgcaaggtca gaggacatgc         960
cttttagccc caaagcatct gttgctgcta tggaagcaaa agaacagttg tctgcacaag        1020
aacttatgga aagtggactg cagattcaga agtcaccaga gcctgaggtt ttgtcaactc        1080
aggaagactt gtttgaccag agcaataaaa cagtatcttc tgatggttgc tctactcctt        1140
caagggagga aggtggggtgt tctttggctt ccactcctgc caccactctg catctcctgc       1200
agctctctgg tcagaggtcc cttgttcagg acagtctttc cacgaattct tcagatcttg       1260
```

```
ttgctccttc tcctgatgct ttccgatcta ctccttttat cgttcctagc agtcccacag   1320
agcaagaagg gagacaagat aagccaatgg acacgtcagt gttatctgaa gaaggaggag   1380
agccttttca gaagaaactt caaagtggtg aaccagtgga gttagaaaac cccctctcc    1440 tgcctgagtc cactgtatca ccacaagcct caacaccaat atctcagagc acaccagtct   1500
tccctcctgg gtcacttcct atcccatccc agcctcagtt ttctcatgac atttttattc   1560
cttccccaag tctggaagaa caatcaaatg atgggaagaa agatggagat atgcatagtt   1620
catctttgac agttgagtgt tctaaaactt cagagattga accaaagaat tcccctgagg   1680
atcttgggct atctttgaca ggggattctt gcaagttgat gctttctaca agtgaatata   1740
gtcagtcccc aaagatggag agcttgagtt ctcacagaat tgatgaagat ggagaaaaca   1800
cacagattga ggatacggaa cccatgtctc cagttctcaa ttctaaattt gttcctgctg   1860
aaaatgatag tatcctgatg aatccagcac aggatggtga agtacaactg agtcagaatg   1920
atgacaaaac aaagggagat gatacagaca ccagggatga cattagtatt ttagccactg   1980
gttgcaaggg cagagaagaa acggtagcag aagatgtttg tattgatctc acttgtgatt   2040
cggggagtca ggcagttccg tcaccagcta ctcgatctga ggcactttct agtgtgttag   2100
atcaggagga agctatggaa attaaagaac accatccaga ggagggtct tcagggtctg    2160 aggtggaaga atccctgag acaccttgtg aaagtcaagg agaggaactc aaagaagaaa    2220
atatggagag tgttccgttg cacctttctc tgactgaaac tcagtcccaa gggttgtgtc   2280
ttcaaaagga aatgccaaaa aaagaatgct cagaagctat ggaagttgaa accagtgtga   2340
ttagtattga ttcccctcaa aagttggcaa tacttgacca agaattggaa cataaggaac   2400
aggaagcttg ggaagaagct acttcagagg actccagtgt tgtcattgta gatgtgaaag   2460
agccatctcc cagagttgat gtttcttgtg aacctttgga gggagtggag aagtgctcag   2520
attcccagtc atgggaggat attgctccag aaatagaacc atgtgctgag aatagattag   2580
acaccaagga agaaaagagt gtagaatatg aaggagatct gaaatcaggg actgcagaaa   2640
cagaacctgt agagcaagat tcttcacagc cttccttacc tttagtgaga gcagatgatc   2700
ctttaagact tgaccaggag ttgcagcagc cccaaactca ggagaaaaca agtaattcat   2760
taacagaaga ctcaaaaatg gctaatgcaa agcagctaag ctcagatgca gaggcccaga   2820
agctggggaa gccctctgcc catgcctcac aaagcttctg tgaaagttct agtgaaaccc   2880
catttcattt cactttgcct aaagaaggtg atatcatccc accattgact ggtgcaaccc   2940
cacctcttat tgggcaccta aaattggagc ccaagagaca cagtactcct attggtatta   3000
gcaactatcc agaaagcacc atagcaacca gtgatgtcat gtctgaaagc atggtggaga   3060
cccatgatcc catacttggg agtggaaaag gggattctgg ggctgcccca gacgtggatg   3120
ataaattatg tctaagaatg aaactggtta gtcctgagac tgaggcgagt gaagagtctt   3180
tgcagttcaa cctggaaaag cctgcaactg gtgaaagaaa aatggatctc actgctgttg   3240
ctgagtctgt tgccagtccc cagaagacca tgtctgtgtt gagctgtatc tgtgaagcca   3300
ggcaagagaa tgaggctcga agtgaggatc cccccaccac acccatcagg gggaacttgc   3360
tccactttcc aagttctcaa ggagaagagg agaaagaaaa attggagggt gaccatacaa   3420
tcaggcagag tcaacagcct atgaagccca ttagtcctgt caaggaccct gtttctcctg   3480
cttcccagaa gatggtcata caagggccat ccagtcctca aggagaggca atggtgacag   3540
atgtgctaga agaccagaaa gaaggacgga gtactaataa ggaaaatcct agtaaggcct   3600
```

```
tgattgaaag gcccagccaa aataacatag gaatccaaac catggagtgt tccttgaggg   3660
tcccagaaac tgtttcagca gcaacccaga ctataaagaa tgtgtgtgag caggggacca   3720
gtacagtgga ccagaacttt ggaaagcaag atgccacagt tcagactgag agggggagtg   3780
gtgagaaacc agtcagtgct cctggggatg atacagagtc gctccatagc cagggagaag   3840
aagagtttga tatgcctcag cctccacatg gccatgtctt acatcgtcac atgagaacaa   3900
tccgggaagt acgcacactt gtcactcgtg tcattacaga tgtgtattat gtggatggaa   3960
cagaagtaga aagaaaagta actgaggaga ctgaagagcc aattgtagag tgtcaggagt   4020
gtgaaactga agtttcccct tcacagactg ggggctcctc aggtgacctg ggggatatca   4080
gctccttctc ctccaaggca tccagcttac accgcacatc aagtgggaca agtctctcag   4140
ctatgcacag cagtggaagc tcaggaaagg agccggacc actcagaggg aaaaccagcg   4200
ggacagaacc cgcagatttt gccttaccca gctcccgagg aggcccagga aaactgagtc   4260
ctagaaaagg ggtcagtcag acaggacgc cagtgtgtga ggaggatggt gatgcaggcc   4320
ttggcatcag acagggaggg aaggctccag tcacgcctcg tgggcgtggg cgaaggggcc   4380
gcccaccttc tcggaccact ggaaccagag aaacagctgt gcctggcccc ttgggcatag   4440
aggacatttc acctaacttg tcaccagatg ataaatcctt cagccgtgtc gtgccccgag   4500
tgccagactc caccagacga acagatgtgg gtgctggtgc tttgcgtcgt agtgactctc   4560
cagaaattcc tttccaggct gctgctggcc cttctgatgg cttagatgcc tcctctccag   4620
gaaatagctt tgtagggctc cgtgttgtag ccaagtggtc atccaatggc tactttttact   4680 ctgggaaaat cacacgagat gtcggagctg ggaagtataa attgctcttt gatgatgggt   4740
acgaatgtga tgtgttgggc aaagacattc tgttatgtga ccccatcccg ctggacactg   4800
aagtgacggc cctctcggag gatgagtatt tcagtgcagg agtggtgaaa ggacatagga   4860
aggagtctgg ggaactgtac tacagcattg aaaaagaagg ccaaagaaag tggtataagc   4920
gaatggctgt catcctgtcc ttggagcaag gaaacagact gagagagcag tatgggcttg   4980 gccctatga agcagtaaca cctcttacaa aggcagcaga tatcagctta gacaatttgg   5040
tggaagggaa gcggaaacgg cgcagtaacg tcagctcccc agccaccct actgcctcca   5100 gtagcagcag cacaacccct acccgaaaga tcacagaaag tcctcgtgcc tccatgggag   5160
ttctctcagg caaaagaaaa cttatcactt ctgaagagga acggtcccct gccaagcgag   5220
gtcgcaagtc tgccacagta aaacctggtg cagtaggggc aggagagttt gtgagcccct   5280
gtgagagtgg agacaacacc ggtgaaccct ctgccctgga agagcagaga gggcctttgc   5340
ctctcaacaa gaccttgttt ctgggctacg catttctcct taccatggcc acaaccagtg   5400
acaagttggc cagccgctcc aaactgccag atggtcctac aggaagcagt gaagaagagg   5460
aggaattttt ggaaattcct ccttccaaca gcagtatac agaatcccag cttcgagcag   5520
gagctggcta tatccttgaa gatttcaatg aagcccagtg taacacagct taccagtgtc   5580
ttctaattgc ggatcagcat tgtcgaaccc ggaagtactt cctgtgcctt gccagtggga   5640
ttccttgtgt gtctcatgtc tgggtccatg atagttgcca tgccaaccag ctccagaact   5700
accgtaatta tctgttgcca gctgggtaca gccttgagga gcaaagaatt ctggactggc   5760
aaccccgtga aatccttc cagaatctga aggtactctt ggtatcagac caacagcaga   5820
acttcctgga gctctggtct gagatcctca tgactggtgg tgcagcctct gtgaagcagc   5880
accattcaag tgcccataac aaagatattg ctttagggt atttgatgtg gtggtgacgg   5940
acccctcatg cccagcctcg gtgctgaagt gtgctgaagc attgcagctg cctgtggtgt   6000
```

```
cacaagagtg ggtgatccag tgcctcattg ttggggagag aattggattc aagcagcatc    6060
caaaatataa acacgattat gtttctcact aaagatactt ggtcttactg gttttattcc    6120
ctgctatcgt ggagattgtg ttttaaccag gtttaaatg tgtcttgtgt gtaactggat     6180
tccttgcatg gatcttgtat atagttttat ttgctgaact tttatgataa aataaatgtt    6240
gaatctcttt ggttgtagta actggg                                         6266
```

METHODS OF IDENTIFYING AN AGENT THAT MODULATES AN INTERACTION BETWEEN 53BP1 AND HISTONE H3, AND USES THEREOF

CROSS REFERENCE TO RELATED APPLICATIONS

This application claims priority to U.S. provisional application 60/620,461, filed Oct. 19, 2004, which is hereby incorporated by reference in its entirety.

GOVERNMENT SUPPORT

This invention was made with U.S. Government support (NCI Grant No. CA76367) and the U.S. Government may therefore have certain rights in the invention.

FIELD OF THE INVENTION

The present invention relates to 53BP1 and histone H3. The present invention also relates to methods of identifying agents that modulate an interaction between 53BP1 and histone H3.

BACKGROUND OF THE INVENTION

Cancer is a significant health problem throughout the world. Although advances have been made in the treatment of cancer, no universally successful method for prevention or treatment is currently available. Cancer therapy currently relies on a combination of early diagnosis and aggressive treatment, which may include radiotherapy, chemotherapy or hormone therapy. The high mortality rate for many cancers indicates that improvements are needed in cancer prevention and treatment.

A wide range of growth factors coordinate cell proliferation and differentiation. Malignant cells arise as a result of a stepwise progression of events that include the unregulated expression of growth factors or components of their signaling pathways. Tyrosine phosphorylation events initiated by receptor, cytoplasmic and nuclear kinases and regulated by phosphatases are central to these processes. Mutation, hyper-activation, translocation and overexpression of protein tyrosine kinases are all associated with tumorigenesis. In addition to increasing proliferative rates and immortalizing cells, overexpression of other oncogenes can lead to morphological transformation and cause anchorage independence, contributing to the promotion of migratory ability and possibly the induction of metastases. Additionally, the inactivation and misregulation of cell cycle checkpoints and tumor suppressors are involved in tumorigenesis.

Cancer chemotherapy ordinarily involves the administration of one or more cytotoxic or cytostatic drugs to a patient. The goal of chemotherapy is to remove a substantially clonal population (tumor) of transformed cells from the body of the individual, or to suppress or to attenuate growth of the tumor. Tumors can occur in solid or liquid form, the latter comprising a cell suspension in blood or other body fluid. A secondary goal of chemotherapy is stabilization (clinical management) of the afflicted individual's health status. Often the tumor may initially respond to chemotherapy but in many instances the initial chemotherapeutic treatment regimen becomes less effective or ceases to inhibit tumor growth. The selection pressure induced by chemotherapy promotes the development of phenotypic changes that allow tumor cells to resist the cytotoxic effects of a chemotherapeutic drug. Often, exposure to one drug induces resistance to that drug as well as other drugs to which the cells have not been exposed.

Cell cycle checkpoints are regulatory systems that control the order and timing of certain events in the cell cycle. These checkpoints are important for ensuring that cells divide properly. For example, DNA damage leads to activation of a cell cycle checkpoint regulatory system that arrests the cell cycle and activates genes involved in repair of DNA damage. This system prevents progression of the cell cycle until the DNA damage has been repaired.

Thus, there is a need to identify factors that are involved in the DNA damage checkpoint pathway as well agents that can modulate the pathway. Agents that can modulate a cell's response to DNA damage may be used to decrease resistance in cancer cells by inhibiting a tumor cell's ability to resist the cytotoxic effects of a chemotherapeutic drug. The present invention satisfies the needs as well as others.

SUMMARY OF THE INVENTION

The present invention provides methods of identifying an agent that modulates an interaction between 53BP1 and Histone H3 (H3). In some embodiments, the methods comprise contacting 53BP1 and H3 in the presence of the agent; and determining whether the agent modulates an interaction between 53BP1 and H3, thereby identifying an agent that modulates an interaction between 53BP1 and H3.

In some embodiments, the present invention provides methods of identifying an agent which modulates a DNA damage response comprising contacting a cell with an agent that modulates an interaction of 53BP1 and histone H3; and determining whether the agent that modulates the interaction of 53BP1 and histone H3 modulates the cell's response to DNA damage.

In some embodiments, the present invention provides methods of identifying an agent that modulates an interaction between 53BP1 or fragment thereof and a methylated peptide that binds to said 53BP1 or fragment thereof comprising contacting 53BP1 or fragment thereof and said methylated peptide in the presence of the agent; and determining whether the agent modulates an interaction between 53BP1 and said methylated peptide, thereby identifying an agent which modulates an interaction between 53BP1 and said methylated peptide.

In some embodiments, the present invention provides methods of treating cancer in an individual comprising administering a 53BP1-H3 inhibitor to the individual.

In some embodiments, the present invention provides methods of inhibiting cancer cell growth comprising contacting the cell with a 53BP1-H3 inhibitor.

In some embodiments, the present invention provides methods of sensitizing a cell to a cancer treatment comprising contacting the cell with a 53BP1-H3 inhibitor.

In some embodiments, the present invention provides compositions comprising a polypeptide comprising a histone H3-binding fragment of 53BP1.

In some embodiments, the present invention provides compositions comprising a methylated peptide comprising a 53BP1-binding fragment of Histone H3.

BRIEF DESCRIPTION OF FIGURES

FIG. 1 Evolutionary conservation and three-dimensional structure of the domain that targets 53BP1 to sites of DNA DSBs. a, Amino acid sequence conservation of residues 1486-1602 of human 53BP1. Conserved residues are colored blue or magenta, depending on whether they appear to contribute to folding or not. Codon numbers above the sequences refer to human 53BP1 and are colored green, red and blue corresponding to the N-terminal tudor fold, C-terminal tudor fold and C-terminal helix, respectively. The secondary structure elements are also indicated above the sequence (s, strand; h, helix). 53BP1hs, human 53BP1; 53BP1xl, *X. laevis* 53BP1; HSR9ce, *C. elegans* Hsr9; RAD9sc, *S. cerevisiae* Rad9; RHP9sp, *S. pombe* Rhp9/Crb2. The sequence alignment was guided by the three-dimensional structure of human 53BP1. b, Stereo ribbons representation of the three-dimensional structure of residues 1486-1602 of human 53BP1. The two tudor folds are colored red (N-terminal) and green (C-terminal) and the C-terminal α-helix is colored blue. The side chains of select residues are also shown. Residues are labeled using the single letter amino acid code and the codon number; for residues with codon numbers 1500-1599, only the last 2 digits of the codon number are shown.

DETAILED DESCRIPTION

Figure 2:
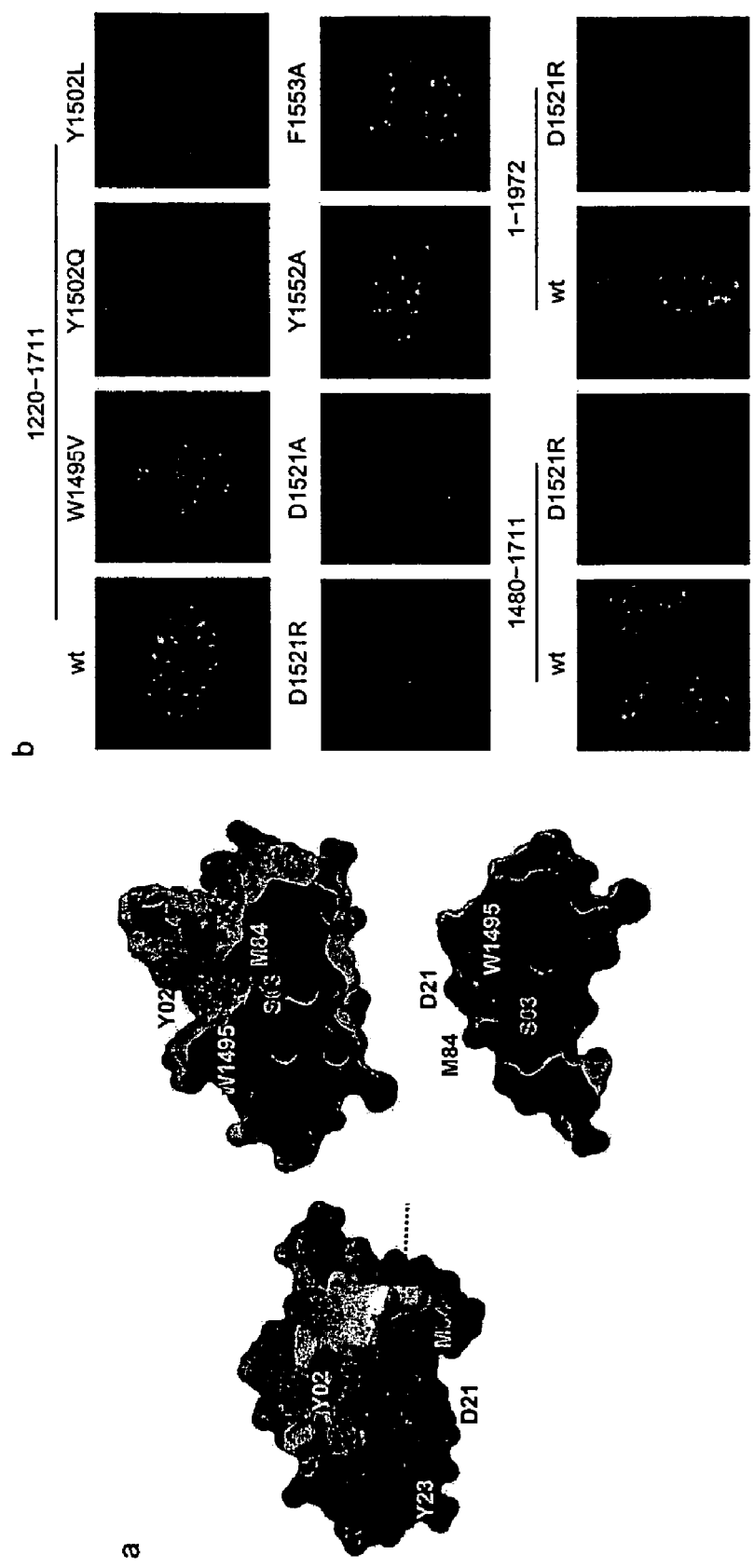
FIG. 2 Mapping functionally important 53BP1 residues on the surface of its tandem tudor domain. a, Left panel: Surface representation of the tandem tudor domain showing a pocket formed by conserved residues. Right panels: Surface representations of the domain sliced along the dotted red line shown in the left panel to reveal the depth of the pocket. The orientation of the domain in the upper panel is the same as shown in FIG. 1. The residues, whose projections are colored on the 53BP1 surface, are labeled as in FIG. 1b. b, Intracellular localization of GFP fused to residues 1220-1711, 1480-1711 or 1-1972 (full-length) of wild-type (wt) or mutant 53BP1 in irradiated cells.

53BP1 is a key transducer of the DNA damage checkpoint signal. 53BP1 is required for phosphorylation of a subset of ATM substrates and p53 accumulation, which are two proteins that are necessary for a functional DNA damage checkpoint. 53BP1 comprises various domains and motifs that are involved in binding other proteins or are modified after a cell is exposed to a DNA damaging agent. For example, the 53BP1 N-terminal region is phosphorylated after a cell is irradiated. The two C-terminal BRCT motifs of 53BP1 interact with p53 and its central region is necessary for 53BP1 foci formation at sites of DNA double strand breaks (DSBs). However, it has not been known how or what 53BP1 binds to form foci at DNA DSBs.

The present invention demonstrates that 53BP1 binds to histone H3 (H3) at sites of DNA DSBs in response to DNA damage (e.g. irradiation). Because localization of 53BP1 to sites of DNA DSBs is expected to be critical to its function, an agent that modulates the interaction of 53BP1 with H3 would modulate 53BP1 function and, accordingly, the response of cells to DNA damage. Further, such agents could be used to modulate the response of normal and cancer cells to many current cancer therapies, because many current cancer therapeutics are DNA damaging agents. In addition, because DNA damage is thought to occur during normal and cancer cell divisions, agents that modulate the interaction of 53BP1 with H3 may even affect cells that are not exposed to DNA damaging agents.

As used herein, the term "about" refers to an amount that is ±10% of the value being modified by the term "about." For example, "about 10" would include at least 9 and up to and including 11.

Accordingly, the present invention provides methods of identifying agents that modulate an interaction between 53BP1 and H3. In some embodiments, the present invention provides methods of identifying agents that modulate a 53BP1-H3 mediated cellular event. In some embodiments, the method comprises contacting 53BP1 and H3 in the presence of the agent and determining whether the agent modulates an interaction between 53BP1 and H3. If the agent modulates an interaction between 53BP1 and H3, this method would thereby identify the agent as a modulator of an interaction between 53BP1 and H3. In some embodiments, the method comprises contacting 53BP1 and H3 with an agent under conditions that 53BP1 and h3 can bind to one another.

As used herein, the term "agent" refers to any compound or composition that can be tested as potential modulator of an interaction between 53BP1 and H3 or any binding partner of 53BP1, such as, but not limited to a methylated peptide. Examples of agents that can be used include, but are not limited to, a small organic molecule, an antibody, antibody fragment, siRNA, nucleic acid molecule (RNA or DNA), antisense oligonucleotide, peptide, peptide mimetic, and the like. In some embodiments, an agent can be isolated or not isolated. As a non-limiting example, an agent can be a library of agents that are used in the present invention to determine if they are a modulator of an interaction between 53BP1 and its binding partner. If a mixture of agents is found to be a modulator, the pool can then be further purified into separate components to determine which components are in fact modulators of an interaction between 53BP1 and its binding partner, such as H3 or a fragment thereof or a methylated peptide.

In some embodiments, H3 or a fragment there of is methylated.

As used herein, the term "contacting" refers to the bringing together or combining of molecules such that they are within a distance for allowing of intermolecular interactions such as the non-covalent interaction between a two proteins or one protein and a modulator. In some embodiments, contacting occurs in solution phase in which the combined or contacted molecules are dissolved in a common solvent and are allowed to freely associate. In some embodiments, the contacting can occur within a cell or in a cell-free environment. In some embodiments, the cell-free environment is the lysate produce from a cell. In some embodiments, a cell lysate may be a whole-cell lysate, nuclear lysate, cytoplasm lysate, and combinations thereof. In some embodiments, the cell-free lysate is only lysate obtained from a nuclear extraction and isolation wherein the nuclei of a cell population are removed from the cells and then lysed. In some embodiments, the nuclei are not lysed, but are still considered to be a cell-free environment.

As used herein, the term "modulates" refers to an increase or decrease in a cellular event or interaction that can be measured. A "cellular event" can refer to changes in a protein's phosphorylation, changes in RNA expression, changes in protein expression, changes in protein interactions, and the like. An interaction can be, for example, binding of one protein to another.

As used herein, the term "a 53BP1-H3 mediated cellular event" refers to a cellular event that is modulated (increased or decreased) in response to 53BP1 binding to H3.

As used herein, the term "an interaction between 53BP1 and H3" refers to any interaction between 53BP1 and H3. In some embodiments, the interaction is direct in that 53BP1 interacts directly with H3. In some embodiments, an interaction between 53BP1 and H3 is non-covalent. In some embodiments, a direct interaction between 53BP1 and H3 or other peptides, such as, but not limited to methylated peptides, is referred to as binding.

In some embodiments, the method comprises comparing an interaction between 53BP1 and H3 or other binding partner of 53BP1 in the presence of the agent and in the absence of the agent. If the agent increases an interaction between 53BP1 and H3 or other binding partner of 53BP1 then the agent is said to be an enhancer. If the agent decreases an interaction between 53BP1 and H3 or other binding partner of 53BP1 then the agent is said to be an inhibitor.

In some embodiments, the agent is contacted with a cell that is expressing 53BP1 and H3. In some embodiments, 53BP1 and H3 or other binding partner of 53BP1 are contacted with an agent in a cell-free environment. In some embodiments, the 53BP1 and H3 or other binding partner of 53BP1 are expressed naturally in a cell, but 53BP1, H3, or other binding partner of 53BP1, or combinations thereof can be expressed exogenously in a cell. As used herein, the term "expressed exogenously" refers to the introduction of genetic material (DNA or RNA) that can drive the expression of a particular gene sequence that encode a polypeptide (e.g. 53BP1 or H3). In some embodiments, 53BP1, H3 or other binding partner of 53BP1 are expressed in a cell by using a plasmid that has been transfected into a cell transiently. In some embodiments, a virus comprising a nucleic acid molecule that encodes for 53BP1, H3 or other binding partner of 53BP1 can be used to infect a cell to exogenously express 53BP1, H3 or other binding partner of 53BP1. In some embodiments, a cell is stably transfected with a plasmid or infected with a viral vector to exogenously express 53BP1, H3 or other binding partner of 53BP1, or combinations thereof.

"Other binding partners of 53BP1" include, but is not limited to methylated peptides. As discussed herein and below, the methylated peptide can be derived from histones (e.g. histone H3 and histone H4) or from other proteins, or synthesized de novo.

As described herein, 53BP1 interacts with H3 through a methylated lysine residue on H3. Accordingly, an agent that can be used is a peptide fragment of H3 that is able to bind to 53BP1. In some embodiments, the H3 peptide is a methylated peptide. In some embodiments, the methylated peptide is monomethylated, dimethylated, or trimethylated. In some embodiments, the H3 peptide is about 3, about 5, about 10, about 15, about 20, about 30, about 40, about 50, about 60, about 70, about 80 amino acid residues in length. In some embodiments, the H3 peptide is from about 5 to about 50, from about 5 to about 40, from about 5 to about 30, from about 5 to about 20, from about 5 to about 15, from about 5 to about 12, from about 5 to about 10 amino acid residues in length. In some embodiments, the H3 peptide is 10 amino acid residues in length. In some embodiments, the H3 peptide comprises amino acid residues 74-83 of H3 (SEQ ID NO:2). In some embodiments, the H3 peptide comprises amino acid residues 73-81 of H3. In some embodiments, the H3 peptide is methylated at a position that corresponds to residue 79 of H3. In some embodiments, the residue is monomethylated, dimethylated, or trimethylated.

A position that corresponds to residue 79 of H3 can be determined by using any alignment software that allows one to compare one amino acid sequence with another. Programs that perform alignments are well known to one of ordinary skill in the art and do not involve undue experimentation. For example, one of skill in the art can use a bioinformatics programs such as MacVector® or DS Gene (Available from Accelrys, San Diego, Calif., USA), but any program can be used.

As used herein the term "53BP1" refers to a protein comprising an amino acid sequence as described in SEQ ID NO: 1. In some embodiments, 53BP1 refers to an amino acid sequence that is homologous to SEQ ID NO:1. In some embodiments, the sequence is at least 15%, at least 20%, at least 30%, at least 40%, at least 50%, at least 60%, at least 70%, at least 80%, at least 90%, at least 95%, or at least 99% homologous to SEQ ID NO:1. In some embodiments, the sequence is at least 15%, at least 20%, at least 30%, at least 40%, at least 50%, at least 60%, at least 70%, at least 80%, at least 90%, at least 95%, or at least 99% identical to SEQ ID NO:1. 53BP1 is well conserved through evolution with homologues existing in yeast, mouse and rats. Any homologue of 53BP1 can be used. For example, the yeast homologue of 53BP1, rad9, can be used to identify an agent that modulates an interaction between 53BP1 and H3. As described herein, S. cerevisiae Rad9 (homologue of 53BP1) interacts with histone H3 even though the domains that are responsible for binding to H3 in Rad9 and 53BP1 are only 20.9% identical.

According to some embodiments a homologous peptide refers to a peptide that has conservative substitutions. A conservative substitution is recognized in the art as a substitution of one amino acid for another amino acid that has similar properties. In some embodiments examples of conservative substitutions are those that are described in Table 1.

TABLE 1

| Amino Acid | Conservative Changes |
| --- | --- |
| Alanine (A) | Glycine (G), Serine (S) |
| Aspartic Acid (D) | Glutamic Acid (E) |
| Glutamic Acid (E) | Aspartic Acid (D) |
| Phenylalanine (F) | Tryptophan (W), Tyrosine (Y) |
| Glycine (G) | Alanine (A) |
| Histidine (H) | Tyrosine (Y) |
| Isoleucine (I) | Leucine (L), Methionine (M), Valine (V) |
| Lysine (K) | Arginine (R) |
| Leucine (L) | Isoleucine (1), Methionine (M) Valine (V) |
| Methionine (M) | Isoleucine (1), Leucine (L), Valine (V) |
| Asparagine (N) | Glutamine (Q) |
| Glutamine (Q) | Asparagine (N) |
| Arginine (R) | Lysine (K) |
| Serine (S) | Alanine (A), Threonine (T) |
| Threonine (T) | Serine (S) |
| Valine (V) | Isoleucine (I), Methionine (M) Valine (V) |
| Tryptophan (W) | Phenylalanine (F), Tyrosine (Y) |
| Tyrosine (Y) | Phenylalanine (F) Histidine (H) Tryptophan (W) |

As used herein, the phrase "homologous", "homologous peptide", "homologous peptide thereof" or variations thereof, refers to sequences characterized by a homology, at the nucleotide level or amino acid level, of at least a specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals and yeast. Homologous nucleotide sequences also include, but are not limited to, naturally occurring allelic variations and mutations of the nucleotide sequences that encode for a homologous polypeptide. Homologous amino acid sequences include those amino acid sequences which contain conservative amino acid substitutions and which polypeptides have the same binding and/or activity.

Percent homology, similarity, or identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology between the probe and target is between about 50% to about 60%. In some embodiments, nucleic acids have nucleotides that are about 60%, preferably about 70%, more preferably about 80%, more preferably about 85%, more preferably about 90%, more preferably about 92%, more preferably about 94%, more preferably about 95%, more preferably about 97%, more preferably about 98%, more preferably about 99% and most preferably about 100% homologous to nucleotide sequences disclosed herein.

Homology may also be at the polypeptide level. In some embodiments, polypeptides are about 20%, about 30%, about 40%, about 50%, about 60%, about 70%, about 80%, about 85%, about 90%, about 92%, about 94%, about 95%, about 97%, about 98%, about 99% or about 100% homologous to the polypeptide sequences disclosed herein. Homologous polypeptide sequences include polypeptide sequences of a species other than humans, including, but not limited to, mammals, yeast, and the like. Homologous polypeptide sequences also include, but are not limited to, naturally occurring allelic variations and mutations of the polypeptide sequences set forth herein. Homologous amino acid sequences include those amino acid sequences which contain conservative amino acid substitutions and which polypeptides have the same binding and/or activity.

In some embodiments the H3 peptides have non-conservative amino acid substitutions of residues that do not directly contact 53BP1. For example a variant of a peptide corresponding to residues 73-81 of H3 has the residue corresponding to Ile74 in the natural H3 sequence (SEQ ID NO:2) substituted with Ala. The side chain of said Ile74 is not solvent-exposed in the folded H3 structure (ref. 27) and therefore cannot contact 53BP1. In some embodiments, non-conservative substitutions of the type described here can be used because they can affect the solubility of the peptide or its cell-permeability or the conformation and/or flexibility of its backbone.

In some embodiments, a fragment of 53BP1 can be a histone H3-binding fragment of 53BP1. As used herein, the term "H3-binding fragment of 53BP1" refers to fragment of 53BP1 that can still bind to H3. In some embodiments, a H3-binding fragment of 53BP1 comprises from about 120 to about 1000, from about 120 to about 800, from about 120 to about 600, from about 120 to about 500, from about 120 to about 400, from about 120 to about 300, from about 120 to about 250, from about 120 to about 200, from about 120 to about 150 amino acid residues. In some embodiments, the H3-binding fragment of 53BP1 comprises residues 1157-1634, 1480-1626, 1486-1602, 1483-1602, 1220-1711, 1483-1624, 1483-1606, and/or 1480-1711. A 53BP1 protein or fragment thereof can also comprise mutations within 53BP1 or a fragment thereof that may or may not effect the binding of 53BP1 to H3. In some embodiments 53BP1 comprises mutations at position 1495, 1502, 1521, 1552, 1553, or combinations thereof. In some embodiments, 53BP1 comprises a Trp1495Val mutation, Tyr1502(Gln/Lue) mutation, Asp1521(Arg/Ala) mutation, Tyr1552Ala mutation, Phe1553Ala mutation, or combinations thereof.

As used herein, the term "mutation" can refer to a substitution, insertion, deletion, and the like.

As used herein, the term "fragment" refers to a portion of a protein that is less than the entire protein. For example, a fragment of 53BP1 would have at least one amino acid less than what is described in SEQ ID NO:1. In some embodiments, a fragment of a protein is used in the place of the full length protein. For example, in some embodiments, a fragment of H3 or 53BP1 is used.

As used herein, the term Histone H3 (H3) refers to a protein having an amino acid sequence comprising SEQ ID NO:2. H3 can also refer to homologous polypeptides having the same function and activity from other species that are, for example, either *mammalian* or yeast. In some embodiments, a fragment of H3 refers to a 53BP1-binding fragment of histone H3. In some embodiments, a 53BP1-binding fragment of histone H3 comprises from about 5 to about 80, from about 5 to about 50, from about 5 to about 40, from about 5 to about 30, from about 5 to about 20, from about 5 to about 15, from about 5 to about 12, from about 5 to about 10 amino acid residues. In some embodiments, a 53BP1-binding fragment of histone H3 comprises 10 amino acid residues. In some embodiments, a 53BP1-binding fragment of histone H3 comprises residues 74-83, 28-135, 23-34, 23-32, or combinations thereof of SEQ ID NO: 2. In some embodiments, a 53BP1-binding fragment of histone H3 comprises a methylated amino acid residue. In some embodiments, a 53BP1-binding fragment of histone H3 comprises a monomethylated, dimethylated, or trimethylated amino acid residue. In some embodiments, a 53BP1-binding fragment of histone H3 comprises a methylated lysine residue that corresponds to residue 79 of SEQ ID NO:2. In some embodiments, H3 or a 53BP1-binding fragment of histone H3 comprises a mutation. In some embodiments, H3 or a 53BP1-binding fragment of histone H3 comprises a mutation at position that corresponds to position 27, 26, 74, or combinations thereof. In some embodiments, the amino acid that corresponds to position 74 is an alanine residue. In some embodiments H3 or a 53BP1-binding fragment of histone H3 comprises an Ile74Ala mutation.

In some embodiments the 53BP1, histone H3, other binding partner of 53BP1, or combinations thereof are of isolated form. As used herein the term "of isolated form" refers to a form of 53BP1 or H3 that are isolated from its natural source. A peptide is isolated when it is synthesized. In some embodiments, 53BBP1, H3, or both are of purified form. As used herein, the term "purified form" refers to a form that has reduced contaminants as compared to a non-purified form. Purity can be measured by comparing the amount of 53BP1 or H3 protein to the total amount of protein in a sample. The less contaminating protein there is, the more pure the 53BP1 or H3 protein is. In some embodiments, the proteins are 100%, about 90%, about 80%, about 70%, about 60%, about 50%, about 40%, or about 30% pure.

In some embodiments, 53BP1, H3, binding partner of 53BP1, or combinations thereof are immobilized or attached to a surface. In some embodiments, the proteins are immobilized by using an antibody. In some embodiments, proteins are cross-linked to a surface (e.g. glass, plastic, microplate, multiwell plate, chip, or array), molecule, or polypeptide. In some embodiments, the proteins are attached to a conjugate. Examples of conjugates include, but are not limited to biotin.

In some embodiments, the proteins and fragments described herein and used in the present invention are fusion proteins that comprise 53BP1, H3-binding fragment of 53BP1, H3, or a 53BP1-binding fragment of H3. As used herein, the term "fusion protein" refers to a protein that comprises amino acids that are from at least two different proteins. This can also be referred to as a protein or peptide fused in frame with another protein. In some embodiments, the fusion protein comprises GFP fused in frame. In some embodiments, the fusion protein comprises a 6-HIS-tag, myc-tag, or other amino acid tag. In some embodiments, the tag can be used to immobilize or attach the protein to a surface, such as, but not limited to, a column, a slurry of beads, a bottom of a well of a microtiter plate or multiwell plate. In some embodiments, the proteins are labeled. In some embodiments, the proteins are labeled with a fluorescent marker. Fluorescent markers can be used to measure the binding of one protein to another protein or other agent by measuring the changes in excitation or fluorescence of the marker. In some embodiments, the marker is GFP, YFP, and the like.

In some embodiments, the present invention provides methods of identifying an agent that modulates an interaction between 53BP1 or fragment thereof and a methylated peptide that binds to said 53BP1 or fragment thereof. In some embodiments, the method can comprise contacting 53BP1 or fragment thereof and said methylated peptide in the presence of the agent; and determining whether the agent modulates an interaction between 53BP1 and said methylated peptide, thereby identifying an agent which modulates an interaction between 53BP1 and said methylated peptide. In some embodiments, the fragment of 53BP1 is a fragment that binds to Histone H3.

The methylated peptide that binds to 53BP1 or a fragment thereof can be any peptide that is able to bind to 53BP1 and is not restricted to a peptide derived from H3. For example, a peptide comprising a fragment of histone H4 can bind to 53BP1. The binding is not restricted to physiological binding, but can bind in vitro. In some embodiments, a methylated peptide of H4 is used. In some embodiments, the residue in the fragment that is methylated corresponds to the lysine at position 20 of H4. The sequence of H4 is readily known. In some embodiments, the methylated peptide comprises residues 74-83 of histone H3. In some embodiments, the methylated peptide comprises residues 23-34 and 23-32. In some embodiments, the lysine at position 27 and/or the arginine at position 26 is methylated. In some embodiments, the peptide comprises about 7 to about 40 residues, about 8 to about 30, about 9 to about 20, about 8 to about 15, about 8 to about 12, about 10 to about 15, about 10 residues.

In some embodiments, the peptides described herein, including, but not limited to the methylated peptides are labeled with a molecule that facilitates detection or measurement of an interaction. In some embodiments, the label is a fluorescent label or fluorophore. In some embodiments, the peptide comprises a radioactive label.

A "methylated peptide" can comprise be monomethylated, dimethylated, or trimethylated at one or more residues. The degree of methylation refers to the specific residue. For example, a peptide with a lysine that is methylated twice is considered dimethylated at the lysine. However, the peptide can still be methylated at other residues of the peptide or protein.

In some embodiments, a change in interaction between 53BP1 and its binding partner, such as, but not limited to, a methylated peptide or fragment of H3, is determined by measuring changes in fluorescence or radioactivity. For example, if the methylated peptide is fluorescently labeled and bound to 53BP1 or a fragment thereof, an agent that disrupts the interaction will cause a decrease in fluorescence in the complex. Changes in fluorescence can be also be measured by other means included polarimetry and the like. In some embodiments, an increase in fluorescence or polarimetry can indicate a change (increase or decrease) in an interaction between 53BP1 and its binding partner. In some embodiments, a decrease in fluorescence or polarimetry can indicate a change (increase or decrease) in an interaction between 53BP1 and its binding partner. In some embodiments, an increase in radioactivity can indicate a change (increase or decrease) in an interaction between 53BP1 and its binding partner. In some embodiments, a decrease in radioactivity can indicate a change (increase or decrease) in an interaction between 53BP1 and its binding partner.

In some embodiments, the interaction between 53BP1 or a fragment thereof is compared in the presence and absence of the agent that is tested to identify an agent that modulates an interaction between 53BP1 and a methylated peptide.

As discussed herein, 53BP1 is intimately involved in regulating a cell's response to DNA damage that causes double stranded breaks. Accordingly, the present invention provides methods of identifying agents that modulate a DNA damage checkpoint. In some embodiments, the methods comprise contacting a cell with an agent that modulates an interaction of 53BP1 and histone H3; and determining whether the agent that modulates the interaction of 53BP1 and histone H3 modulates the cell's response to DNA damage. In some embodiments, the method comprises comparing the DNA damage checkpoint in the presence of the agent and in the absence of the agent.

In some embodiments, the DNA damage is a double strand break. In some embodiments, a cell is exposed to a DNA damaging factor before an agent is contacted with 53BP1 and H3. In some embodiments, a cell is exposed to a DNA damaging factor after an agent is contacted with 53BP1 and H3. In some embodiments, a cell is exposed to a DNA damaging factor simultaneously as an agent is contacted with 53BP1 and H3. In some embodiments, the DNA damaging factor causes double strand breaks in DNA (e.g. ionizing radiation).

A cell's response to DNA damage can be measured by any means. Examples of how to measure a cell's response to DNA damage are known to one of ordinary skill in the art. Examples of how to measure a cell's response to DNA damage include, but are not limited to, determining cell viability, flow cytometry to monitor progression through the cell cycle, changes in the phosphorylation of proteins, changes in RNA and/or protein levels, changes in protein interactions, and the like.

One of skill in the art can measure an interaction between 53BP1 and Histone H3 by any means. In some embodiments, an interaction that is measured is the binding between 53BP1 and Histone H3. Methods that can be used to measure binding between 53BP1 and Histone H3 include, but are not limited to ELISA, immunoprecipitation, Far Western, changes in fluorescence, Biacore system, and the like. Other methods that can be used are described in Kay B K, Paul J I (High-throughput screening strategies to identify inhibitors of protein-protein interactions. Mol Divers. 1996 February; 1(2):139-40); Cunningham B T et al. (Label-free assays on the BIND system. J Biomol Screen. 2004 September; 9(6):481-90); Pierceall W E et al. (Affinity capillary electrophoresis analyses of protein-protein interactions in target-directed drug discovery. Methods Mol. Biol. 2004; 261:187-98); Gadek T R (Strategies and methods in the identification of antagonists of protein-protein interactions. Biotechniques. 2003 June; Suppl:21-4.); Bergendahl V, Heyduk T, Burgess R R (Luminescence resonance energy transfer-based high-throughput screening assay for inhibitors of essential protein-protein interactions in bacterial RNA polymerase. Appl Environ Microbiol. 2003 March; 69(3):1492-8.); Gadek T R, Nicholas J B. (Small molecule antagonists of proteins. Biochem Pharmacol. 2003 January 1; 65(1):1-8.); Boute N, Jockers R, Issad T. (The use of resonance energy transfer in high-throughput screening: BRET versus FRET. Trends Pharmacol Sci. 2002 August; 23(8):351-4); each of which are hereby incorporated by reference in their entirety.

The present invention also provides for methods of treating cancer in an individual comprising administering a composition comprising a 53BP1-H3 inhibitor to the individual. As used herein, the term "53BP1-H3 inhibitor" refers to an agent that inhibits an interaction between 53BP1 and H3. In some embodiments, the inhibitor inhibits the binding of 53BP1 to H3. In some embodiments, the inhibitor inhibits the binding of 53BP1 to H3 by at least 10%, at least 20%, at least 30%, at least 40%, at least 50%, at least 60%, at least 70%, at least 80%, at least 90%, at least 95%, or 100%. In some embodiments, the inhibitor inhibits the binding of 53BP1 to H3 by about 20 to about 100%, about 50 to about 100%, about 75 to about 100%, about 90 to about 100% about 50 to about 75%, or about 80 to about 100%. The percent inhibition can be determined by comparing the binding of 53BP1 to H3 in the presence and absence of the agent. In some embodiments, the percent inhibition can be determined in a cellular environment or in a cell-free environment.

The present invention also provides methods of inhibiting cancer cell growth comprising contacting a composition comprising a 53BP1-H3 inhibitor with the cell. As used herein, the term "cancer cell" can also be referred to as a "tumor cell." The cancer cell can be of any tissue origin including, but not limited to, breast, ovarian, lung, brain, bone, colon, pancreas, kidney, liver, retina, testis, and the like. The cancer cell can also be a blood-type cancer, such as a leukemia, lymphoma, multiple myeloma, and the like.

As discussed herein, many cancers are resistant or become resistant to treatments. Since the interaction between 53BP1 and H3 is important for the cell's response to DNA damage, the present invention can be used to sensitize a cell that has become resistant to a cancer treatment or enhance the effectiveness of a treatment by using an inhibitor of an interaction between 53BP1 and H3 or an inhibitor of a 53BP1-H3 mediated cellular event. Accordingly, the present invention provides methods of sensitizing a cell to a cancer treatment comprising contacting a cell with a 53BP1-H3 inhibitor. A cancer treatment can be any treatment that is used to treat cancer or inhibit cell growth. Examples of cancer treatments include, but are not limited to chemotherapeutics and non-chemotherapeutics. A chemotherapeutic can be any chemotherapeutic including, but not limited to, those that act as intercalating agents or other nucleotide (e.g. DNA) damaging agents. Non-chemotherapeutics refer to a cancer therapeutic that does not cause DNA damage or that is not an intercalating agent.

In some embodiments, the compositions of the present invention are pharmaceutical compositions. In some embodiments, the compositions can be prepared in dose form by well-known procedures. The compositions can be administered, for example, parenterally (e.g. intravenous drip, subcutaneous, intraperitoneal or intramuscular injection, topically (e.g. ophthalmic, vaginal, rectal, intranasal, transdermal), orally, intramuscularly, subcutaneously, pulmonary administration, or intranasally. For parenteral administration, such as intramuscular injection, the compositions can be combined with a suitable carrier, for example, it may be administered in water, saline, or buffered vehicles with or without various adjuvants or immunostimulating agents such as aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid X, *Corynebacterium parvum, Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.). Compositions for parenteral, intravenous, intrathecal or intraventricular administration may include sterile aqueous solutions which can also contain buffers, diluents and other suitable additives and, in some embodiments, can be sterile and/or pyrogen free.

Formulations for topical administration may include transdermal patches, ointments, lotions, creams, gels, drops, suppositories, sprays, liquids and powders. Conventional pharmaceutical carriers; aqueous, powder or oily base; thickeners and the like can be used. Compositions for oral administration include powders or granules, suspensions or solutions in water or non-aqueous media, capsules, sachets or tablets. Thickeners, flavoring agents, diluents, emulsifiers, dispersing aids or binders may be desirable.

On a per dose basis, the concentration of the composition can range from about 0.015 µg to about 1.5 mg per kilogram per body weight. In some embodiments, a dosage range is from about 1.5 µg/kg to about 0.043 mg/kg of body weight. A suitable dose size in humans can be about 0.1-1 ml, or about 0.1 ml. Accordingly, a dose for intramuscular injection in humans, for example, could comprise 0.1 ml containing 1.5 µg/kg composition.

The dosage administered can also vary and depend upon factors such as: pharmacodynamic characteristics; mode and route of administration; age, health, and weight of the recipient; nature and extent of symptoms; kind of concurrent treatment; and frequency of treatment. Usually, the dosage of an immunogenic composition can be about 1 to 3000 milligrams per 50 kilograms of body weight; 10 to 1000 milligrams per 50 kilograms of body weight; 25 to 800 milligrams per 50 kilograms of body weight. In some embodiments, 8 to 800 milligrams administered to an individual per day in divided doses 1 to 6 times a day, or in sustained release form, is effective to obtain desired results. Formulation of therapeutic compositions and their subsequent administration is believed to be within the skill of those in the art.

The compositions according to the present invention can be administered as a single dose or in multiple doses. The compositions of the present invention can be administered either as individual therapeutic agents or in combination with other therapeutic agents. The treatments of the present invention may be combined with conventional therapies, which may be administered sequentially or simultaneously.

The present invention also provides pharmaceutical compositions that comprise the compositions of the present invention and pharmaceutically acceptable carriers or diluents. The compositions of the present invention may be formulated by one having ordinary skill in the art with compositions selected depending upon the chosen mode of administration. Suitable pharmaceutical carriers are described in Remington's Pharmaceutical Sciences, A. Osol, a standard reference text. In carrying out methods of the present invention, immunogenic and/or antigenic compositions of the present invention can be used alone or in combination with other diagnostic, therapeutic or additional agents. Such additional agents include excipients such as flavoring, coloring, stabilizing agents, thickening materials, osmotic agents and antibacterial agents. Such agents may enhance the lipoparticle use in vitro or in vivo, the stability of the composition during storage, or other properties important to achieving optimal effectiveness.

For parenteral administration, the compositions of the present invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder may contain additives that maintain isotonicity (e.g., sodium chloride, mannitol) and chemical stability (e.g., buffers and preservatives). The formulation can be sterilized by commonly used techniques. For example, a parenteral composition suitable for administration by injection is prepared by dissolving 1.5% by weight of active ingredient in 0.9% sodium chloride solution.

The compositions of the present invention may be administered by any means that enables the active agent to reach the site of action. Because a composition may be subject to being digested when administered orally, parenteral administration, i.e., intravenous, subcutaneous, transdermal, intramuscular, can be used to optimize absorption. Intravenous administration may be accomplished with the aid of an infusion pump. The compositions of the present invention can be formulated as an emulsion. Alternatively, they can be formulated as aerosol medicaments for intranasal or inhalation administration. In some cases, topical administration can be desirable.

Depending upon the disease or disorder to be treated, the compositions of the present invention may be formulated and administered to most effectively to treat the disease or disorder. Modes of administration will be apparent to one skilled in the art in view of the present disclosure.

The present invention also provides for compositions comprising an isolated H3-binding fragment of 53BP1. In some embodiments, the fragment comprises amino acid residues 1157-1634, 1480-1626, 1486-1602, 1483-1602, 1220-1711, 1483-1624, 1483-1606, and/or 1480-1711 of 53BP1 (SEQ ID NO:1). In some embodiments, the compositions comprise a fusion protein comprising a H3-binding fragment of 53BP1. In some embodiments, the fusion protein comprises a fluorescent protein. Examples of fluorescent proteins include, but are not limited to GFP, YFP, and the like. In some embodiments the fusion protein comprises a protein that can bind to a solid support. Examples, of such fusion proteins include, but are not limited to GST, maltose-binding protein, and the like.

The present invention also provides for compositions comprising an isolated methylated peptide comprising a 53BP1-binding fragment of Histone H3. In some embodiments, the 53BP1-binding fragment of Histone H3 comprises a methylated lysine residue that corresponds to residue 79 of histone H3.

In some embodiments, the methylated peptides or proteins described herein or equivalents thereof can be monomethylated, dimethylated, or trimethylated at specific residue, such as a lysine. A peptide or protein or fragment thereof can also be methylated (e.g. monomethylated, dimethylated, or trimethylated) at more than one residue One of skill in the art can determine if a fragment of 53BP1 is a H3-binding fragment of 53BP1 or if a fragment of H3 is a 53BP1-binding fragment of H3 using any means. One can generate fragments of either protein and determine if the fragment is able to bind to the other protein. For example, one of skill in the art can generate a fragment of 53BP1 and then determine if it binds to histone H3 or a fragment of H3. In some embodiments, H3 or a fragment of H3 is methylated for the fragment of 53BP1 to be able to bind to H3 or fragments thereof. If the fragment generated of 53BP1 binds to histone H3 or a fragment thereof, then the fragment of 53BP1 is said to be a H3-binding fragment of 53BP1. The reverse type experiment can also be done to determine if a fragment of Histone H3 can bind to 53BP1 or a fragment thereof.

The present invention also provides for isolated nucleic acid molecules that encode for polypeptides and fragments thereof that are described herein. In some embodiments, the nucleic acid molecule comprises SEQ ID NO: 4: or fragments thereof. In some embodiments, the nucleic acid molecule encodes for a polypeptide comprising amino acid residues 1157-1634, 1480-1626, 1486-1602, 1483-1602, 1220-1711, 1483-1624, 1483-1606, and/or 1480-1711 of 53BP1 (SEQ ID NO:1). In some embodiments, the nucleic acid molecule encodes for a polypeptide comprising residues 74-83, 73-81, or 28-135 of H3 (SEQ ID NO:2). In some embodiments, the nucleic acid molecule is a plasmid or a viral vector (e.g. adenovirus or retrovirus). In some embodiments, the nucleic acid molecule is operably linked to a promoter. According to some embodiments of the present invention, the nucleic acid sequence which encodes for polypeptides described herein or a fragment thereof is operably linked to regulatory elements which are necessary for expression of the sequence in a cell. According to some embodiments of the present invention, the nucleic acid molecule is DNA. In some embodiments, the nucleic acid molecule is free of infectious particles. In some embodiments, the nucleic acid molecule is not a viral particle. In some embodiments, the nucleic acid molecule is combined with a pharmaceutically acceptable carrier or diluent.

The present invention also provides kits comprising one or more of the polypeptides described herein or one or more nucleic acid molecules encoding a polypeptide described herein. The kit can also contain containers and other materials necessary to be used in a method to identify an agent that modulates an interaction between 53BP1 and H3. In some embodiments, the kit comprises an agent that is known to inhibit an interaction between 53BP1 and H3. In some embodiments, the kit comprises H3, 53BP1, or fragments thereof. In some embodiments, the kit comprises at least one solution allow H3 and 53BP1 to bind to one another when H3 and 53BP1 are added to the solution.

EXAMPLES

The invention is now described with reference to the following examples. These examples are provides for the purpose of illustration only and the invention should in now way be construed as being limited to these examples, but rather should be construed to encompass any and all variations which become evident as a result of the teachings provided herein. Those of skill in the art will readily recognize a variety of non-critical parameters that could be changed or modified to yield essentially similar results.

Example 1

The mechanisms by which eukaryotic cells sense the presence of DNA double strand breaks (DSBs) to initiate checkpoint responses are poorly understood. 53BP1, a conserved checkpoint protein, has properties of a DNA DSB sensor[1-5]. The three-dimensional structure of the domain that recruits 53BP1 to sites of DNA DSBs was solved. This domain consists of two tandem tudor folds with a deep pocket at their interface formed by residues conserved in the budding yeast Rad9 and fission yeast Rhp9/Crb2 orthologs. In vitro, the tandem tudor domain of 53BP1 bound histone H3 methylated on Lys79. The residues that form the walls of the conserved pocket were required for binding to methylated histone H3 and also for recruitment of 53BP1 to sites of DNA DSBs. Suppression of Dot1L, the enzyme that methylates histone H3 on Lys79 in vivo, also inhibited recruitment of 53BP1 to sites of DNA DSBs. Because methylation of histone H3 Lys79 was not enhanced in response to DNA damage, we infer that 53BP1 senses DNA DSBs indirectly through changes in higher order chromatin structure that expose the 53BP1-binding site.

The region responsible for recruitment of human 53BP1 to sites of DNA DSBs maps to residues 1480-1616 (ref. 6,7). This region, which is conserved in the 53BP1 putative orthologs in *S. cerevisiae* (Rad9), *S. pombe* (Rhp9/Crb2) and *C. elegans* (Hsr9/TO5F1) (FIG. 1a; ref. 8-11), contains a folded domain (residues 1486-1602 of human 53BP1), whose three-dimensional structure was determined by X-ray crystallography at a resolution of 2.8 Å. The structure, which was also recently solved by NMR spectroscopy[12], revealed that the domain consists of ten β-strands and a C-terminal α-helix (FIG. 1b). The N-terminal 5 β-strands and the C-terminal 5 β-strands adopt folds that are identical to each other and to the fold of the tudor domain of the Survival Motor Neuron (SMN) protein[13,14]. SMN has only one tudor fold, but in 53BP1 two tandem tudor folds comprise a single globular domain.

The residues of 53BP1 that are conserved in the 53BP1/Rad9 family were mapped on the three-dimensional structure. Some of the conserved residues are important for folding. The remaining conserved residues map predominantly to one surface of the domain and mostly to a deep pocket located at the interface of the two tudor folds (FIGS. 1b and 2a). The four walls of this pocket are formed by Trp1495, Tyr1502, Met1584 and Leu1547, and Asp1521, respectively, while the bottom is formed by Ser1503 (FIG. 2a). Thus, the residues lining the walls of this deep pocket are hydrophobic with the exception of Asp1521.

To identify functionally important elements of the 53BP1 tandem tudor domain the structure was utilized to design amino acid substitutions that would change the surface properties of the domain without compromising folding. Trp1495 was substituted with Val; Tyr1502 with Gln or Leu; and Asp1521 with Arg or Ala. In addition, Tyr1552 and Phe1553 were substituted with Ala. The latter two residues are not evolutionarily conserved, but their aromatic side chains are exposed to solvent (FIG. 1b), reminiscent of aromatic residues in single-stranded DNA binding proteins that intercalate between DNA bases[15]. All the substitutions described above were introduced into a fusion protein containing green fluorescent protein (GFP) and residues 1220-1711 of human 53BP1. The ability of these proteins to localize to sites of DNA DSBs was monitored in live cells 15 min after exposure to 3 Gy ionizing radiation (1R). The wild-type 53BP1 fusion protein and the Tyr1552Ala and Phe1553Ala mutants were recruited efficiently to sites of DNA DSBs. In contrast, all the substitutions that targeted the pocket at the interface of the tudor folds compromised or abolished recruitment of 53BP1 to sites of DNA DSBs (FIG. 2b). The effect of the Asp1521Arg substitution was further examined in the context of a GFP-53BP1 fusion that contains just the tudor domain and nuclear localization signal of 53BP1 (residues 1480-1711) and in the context of GFP fused to full-length 53BP1 (residues 1-1972). In both cases the Asp1521Arg substitution abolished recruitment to sites of DNA DSBs (FIG. 2b). The effect of the various amino acid substitutions was not due to unfolding of the tudor domain, as ascertained by gel filtration analysis of purified wild-type and mutant polypeptides expressed in E. coli (data not shown). Therefore, the deep pocket at the interface of the two tudor folds is the critical structural element for targeting 53BP1 to sites of DNA DSBs.

Figure 3:
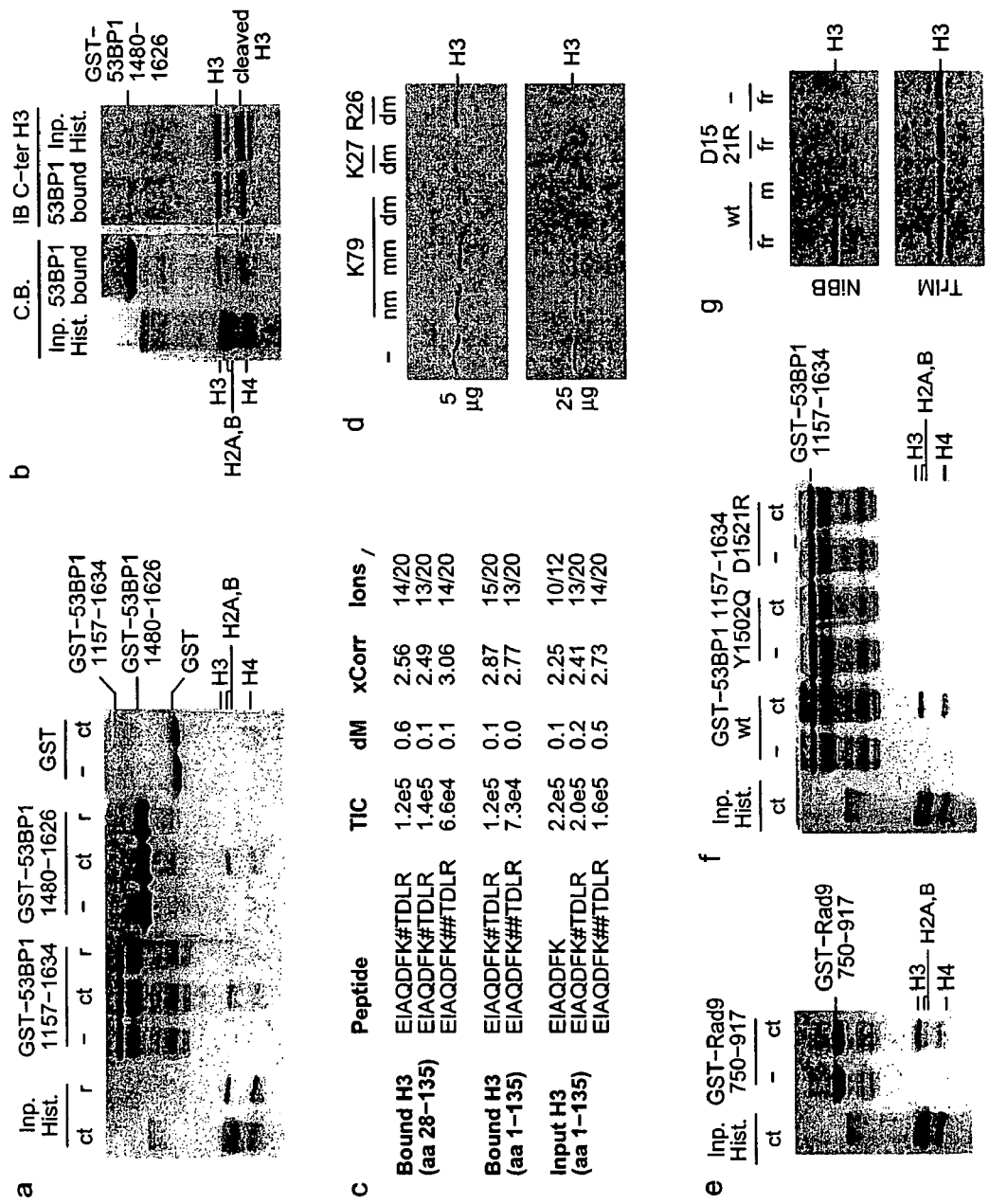
FIG. 3 Binding of the tandem tudor domain of 53BP1 to histone H3 methylated on Lys79. a, GST-53BP1 fusion proteins containing residues 1157-1634 or 1480-1626 of human 53BP1 or plain GST protein were examined for binding to calf thymus histones (ct) or recombinant histones H3 and H4 (r). The proteins were resolved by SDS-PAGE and stained with Coomassie Brilliant Blue. The labels for H3, H2A, H2B and H4 refer to the input histones (Inp. Hist.). b, Identification of 53BP1-bound histones as full-length and N-terminally-cleaved histone H3. Input and GST-53BP1-bound histones were stained with Coomassie Brilliant Blue (C.B.) or immunoblotted (IB) with an antibody that recognizes the C-terminus (C-ter) of histone H3. c, Enrichment for methylation of Lys79 in histone H3 bound to GST-53BP1 as compared to input histone H3. Bound full-length histone H3 (aa 1-135), bound cleaved histone H3 (aa 28-135) and full-length histone H3 from the input fraction were analyzed by tandem mass spectrometry (MS/MS). For each sample, the identified peptides that include Lys79 are shown. K, K# and K## represent non-, mono- and di-methylated lysine, respectively. TIC, total ion current (an indicator of peptide abundance); dM, absolute difference of the experimental and theoretical masses; xCorr, cross correlation value of the experimental MS/MS spectrum versus the theoretical; Ions, number of matched ions in the experimental MS/MS spectrum versus the total number of theoretically possible ions. d, Competition of binding of 53BP1 to histone H3 by methylated histone H3 peptides. Binding of a GST-53BP1 fusion protein containing 53BP1 residues 1480-1626 to histones prepared from 293T cells was performed in the presence of no competitor peptide (−) or 5 or 25 μg histone H3 peptides. Bound histone H3 was detected by immunoblotting. Peptides spanning residues 74-83 of histone H3 had either non- (nm), mono- (mm) or di-methylated (dm) Lys79 (K79); peptides spanning residues 23-34 and 23-32 of histone H3 had dimethylated Lys27 (K27) and Arg26 (R26), respectively. e, Binding of a GST fusion protein containing *S. cerevisiae* Rad9 residues 750-917 to histone H3. Binding was examined as in a. f, Amino acid substitutions that disrupt recruitment of 53BP1 to sites of DNA DSBs also disrupt binding to histone H3. Binding was examined as in a. g, Crosslinking of ectopically-expressed His-tagged GFP-53BP1 to endogenous histone H3 in irradiated U2OS cells. Non-transfected U2OS cells (−) or cells transfected with His-tagged GFP-53BP1 fusion proteins having wild-type (wt) or mutant (Asp1521Arg, D1521R) 53BP1 were crosslinked with formaldehyde (fr) or were mock-crosslinked (m). Triton-X100 insoluble material (TrIM) from these cells was incubated with nickel-coated beads. Histone H3 in the TrIM and nickel bead-bound (NiBB) fractions was detected by immunoblotting after the crosslinks were reversed.

The tudor domain of SMN interacts with methylated arginines present in spliceosomal Sm proteins[13,14,16,17]. Therefore it is reasoned that the deep pocket of 53BP1 might interact with methylated arginines or lysines, in which case, the physiologically-relevant binding partners of 53BP1 might be methylated histones[18]. To explore this hypothesis it was examined if 53BP1 would bind to calf thymus histones. Histones H2A, H2B, H3 and H4 were all present in the input fraction, but 53BP1 bound predominantly to histone H3 (FIG. 3a). The interaction was observed under stringent conditions (1 M KCl and 0.5% Triton X-100) and involved amounts of histone H3 that were readily detected by Coomassie Brilliant Blue staining. A second protein that migrated slightly slower than histone H4 also bound human 53BP1 (FIG. 3a). N-terminal amino acid sequencing and immunoblotting with various histone H3-specific antibodies revealed that this protein was a cleaved form of histone H3 corresponding to residues 28-135 of the full-length protein (FIG. 3b and data not shown). Cleaved histone H3 was also present in the input fraction (FIG. 3b).

Unlike calf thymus histone H3, bacterially-expressed histone H3 failed to interact with 53BP1, suggesting that binding required histone H3 to be posttranslationally modified (FIG. 3a). To identify the relevant posttranslational modification(s) tryptic peptides of 53BP1-bound full-length and cleaved histone H3 were compared by tandem mass spectrometry to tryptic peptides of full-length histone H3 from the input fraction. The only posttranslational modification identified in the 53BP1-bound cleaved histone H3 was methylation of Lys79. Peptides with non-methylated Lys79 were not detected in this sample. Lys79 was also exclusively methylated in the full-length histone H3 bound to 53BP1, whereas non-methylated Lys79 was readily detectable in histone H3 from the input fraction (FIG. 3c). These results suggest that 53BP1 recognizes histone H3 methylated on Lys79. Indeed, a synthetic peptide corresponding to residues 74-83 of human histone H3 with dimethylated Lys79 competed for binding of histone H3 to 53BP1. The corresponding non-methylated peptide did not compete, whereas the monomethylated Lys79 peptide and peptides with dimethylated Lys27 or Arg26 competed with lower efficiency (FIG. 3d). Binding of the 53BP1 tandem tudor domain to a histone H3 peptide with dimethylated Lys79 was also demonstrated by isothermal titration calorimetry, which showed a dissociation constant below 1 μM (data not shown).

If binding to histone H3 was important for recruitment of 53BP1 to sites of DNA DSBs, then the interaction should be conserved in evolution. Further, 53BP1 mutants that fail to localize to sites of DNA DSBs should not interact with histone H3. Both predictions were true. The S. cerevisiae Rad9 DNA damage checkpoint protein, which has the least sequence similarity to human 53BP1 among all 53BP1/Rad9 family members (FIG. 1a), interacted with histone H3 (FIG. 3e). Further, the amino acid substitutions that inhibited recruitment of 53BP1 to sites of DNA DSBs (FIG. 2b) also inhibited binding to histone H3 (FIG. 3f).

The interaction between 53BP1 and histone H3 could also be demonstrated in vivo by crosslinking. Non-transfected U2OS osteosarcoma cells and transfected U2OS cells expressing His-tagged GFP-53BP1 fusion proteins with wild-type or mutant (Asp1521Arg) 53BP1 sequences were pre-extracted with Triton-X100 in situ 15 min after irradiation and then treated with formaldehyde to crosslink interacting proteins. His-tagged GFP-53BP1 was then affinity-purified on nickel-coated beads and bound histone H3 was detected by immunoblotting after the crosslinks were reversed by boiling. Histone H3 was captured on beads incubated with extracts from His-tagged GFP-wild-type 53BP1 expressing cells treated with formaldehyde, but not on beads incubated with extracts from cells that were mock-crosslinked or that were expressing the Asp1521Arg mutant protein (FIG. 3g). Further, the crosslinking was specific for histone H3, because histone H2A, although present in the Triton-X100 insoluble material, was not captured by the beads (data not shown).

Figure 4:
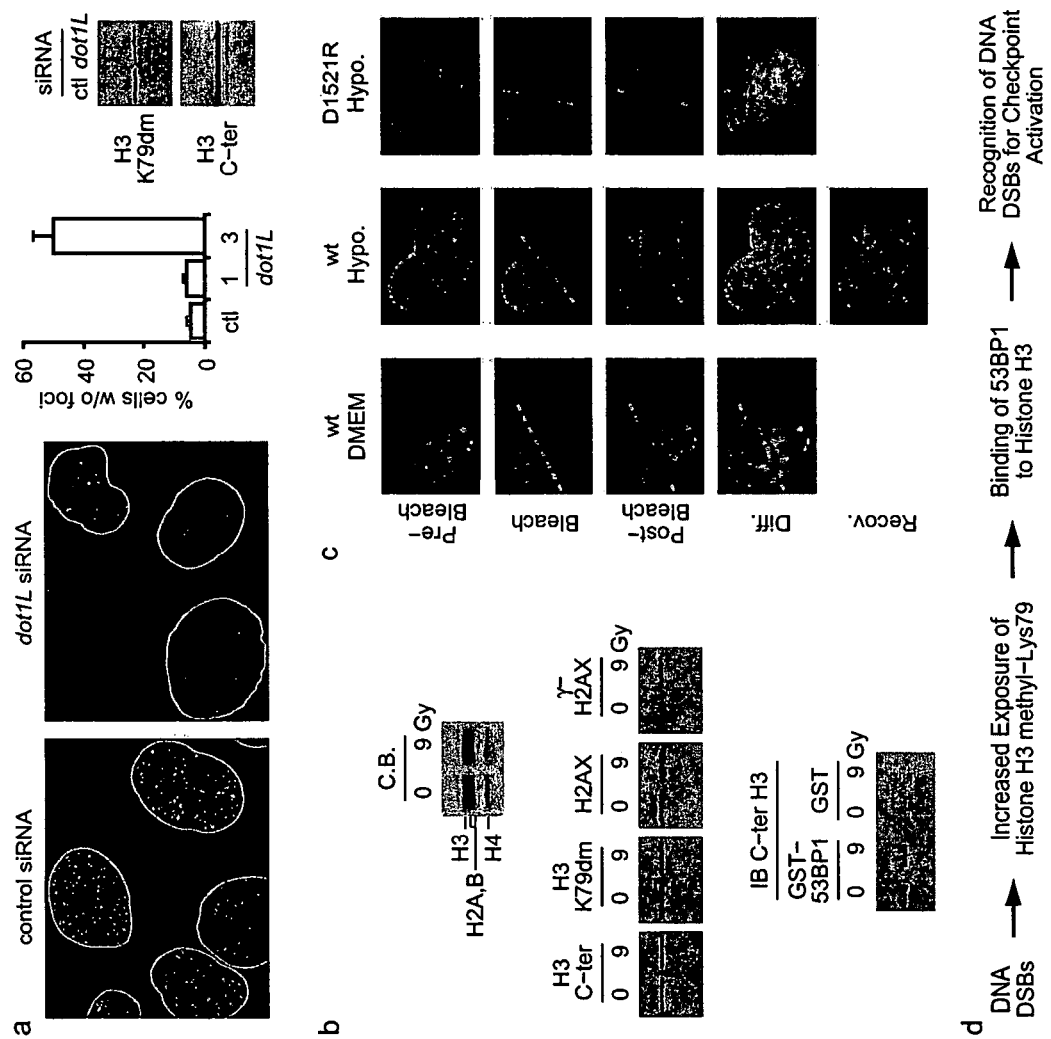
FIG. 4 Histone H3 methylated on Lys79 and changes in higher order chromatin structure recruit 53BP1 to sites of DNA DSBs and chromatin. a, Suppression of histone H3 methylation on Lys79 inhibits recruitment of 53BP1 to sites of DNA DSBs. The percentage of irradiated (9 Gy) U2OS cells without (w/o) 53BP1 foci was determined from 4 independent experiments of control (ctl) siRNA-treated cells or cells transfected once (1) or 3 consecutive times (3) with dot1L-specific siRNA. Bars indicate standard errors. The efficiency of suppression of histone H3 methylation on Lys79 after the third round of dot1L siRNA transfection was monitored by immunoblotting with antibodies that recognize the C-terminus (C-ter) of histone H3 or histone H3 dimethylated on Lys79 (K79dm). b, Irradiation does not enhance methylation of Lys79 of histone H3 or binding of extracted histone H3 to GST-53BP1. Histones prepared from non-irradiated or irradiated (9 Gy) 293T cells were resolved by SDS-PAGE and stained with Coomassie Brilliant Blue (C.B.; top panel) or immunoblotted with antibodies that recognize the C-terminus (C-ter) of histone H3, histone H3 dimethylated on Lys79 (K79dm), histone H2AX and phosphorylated histone H2AX (γ-H2AX; middle panel). The histones from the non-irradiated and irradiated cells were also examined for binding to a GST-53BP1 fusion protein containing residues 1480-1626 of human 53BP1 and to plain GST, as a control. Bound histone H3 was detected by immunoblotting (IB; lower panel). c, Exposure of cells to hypotonic media slows the nuclear diffusion of 53BP1. Cells expressing GFP fused to residues 1220-1711 of 53BP1 that were cultured in regular or hypotonic media were photographed (pre-bleach image), then a portion of their nucleus (bleach image) was bleached for 10 min and another image (post-bleach) was acquired at the end of the bleach period. To show differences in GFP-53BP1 fluorescence before and after bleaching, the post-bleach image was pseudocolored magenta and merged with the pre-bleach image (Diff. image). The GFP-wild-type 53BP1 expressing cells exposed to hypotonic media were allowed to recover from the photobleaching for 7 min and then another image was acquired (Recov. image). Note that the cells cultured in hypotonic media have altered nuclear architecture, as indicated by the morphology of the nucleoli. d, Model for recognition of DNA DSBs by 53BP1.

If 53BP1 is recruited to sites of DNA DSBs by interacting with histone H3 methylated on Lys79, then in the absence of Lys79 methylation 53BP1 would fail to form IR-induced foci. The enzyme that methylates Lys79 in human cells is Dot1L, an evolutionarily conserved methyltransferase[19-21]. Using siRNA specific for human Dot1L we suppressed methylation of histone H3 on Lys79 and also recruitment of 53BP1 to sites of DNA DSBs (FIG. 4a). We did not examine if Dot1L suppression led to checkpoint defects, because the formation of 53BP1 foci was not suppressed in all cells (presumably due to incomplete suppression of Lys79 methylation). However, deletion of dot1 in *S. cerevisiae* leads to radiation sensitivity and a DNA DSB checkpoint defect[22,23]. At least the radiation sensitivity is due to loss of histone H3 Lys79 methylation, because substitution of Lys79 with Ala, Gln or Pro has the same phenotype as deletion of dot1 (ref. 22).

The interaction between 53BP1 and histone H3 methylated on Lys79 suggests two possibilities regarding how 53BP1 is recruited to sites of DNA DSBs; either Lys79 becomes methylated at sites of DNA DSBs or Lys79 is constitutively methylated and its accessibility to 53BP1 changes in response to DNA damage. To distinguish between these possibilities we prepared histones from non-irradiated and irradiated 293T human carcinoma cells. Irradiation did not lead to enhanced methylation of Lys79 of histone H3, even though phosphorylation of histone H2AX, a known marker of irradiation[24], was enhanced (FIG. 4b). Further, histone H3 prepared from irradiated and non-irradiated cells bound equally well to 53BP1 in vitro (FIG. 4b). These results suggest that increased exposure of pre-existing methylated Lys79, rather than newly methylated Lys79, accounts for recruitment of 53BP1 to sites of DNA DSBs.

Increased exposure of pre-existing methylated Lys79 could be due to changes in higher order chromatin structure. Indeed, it has been proposed that DNA DSBs induce long-range changes in chromatin structure, perhaps as a result of relaxation of DNA supercoiling induced by the break[25]. One of the agents that affects chromatin structure and activates the DNA DSB checkpoint kinase ATM without inducing DNA breaks is mild hypotonic media[25]. To explore whether changes in chromatin structure are sufficient to target 53BP1 to chromatin, U2OS osteosarcoma cells expressing GFP fused to residues 1220-1711 of 53BP1 were incubated in regular tissue culture media or for 1 h in hypotonic media and nuclear diffusion of GFP-53BP1 was monitored by photobleaching. It was expected that changes in higher order chromatin structure would target GFP-53BP1 to chromatin and slow its diffusion through the nucleus. A portion of the nucleus of a live cell was bleached with light over a period of 10 min and GFP-53BP1 fluorescence was examined immediately thereafter. In the control cells GFP-53BP1 fluorescence was equal in the bleached and non-bleached areas indicating fast kinetics of 53BP1 diffusion during bleaching, whereas in the cells exposed to hypotonic media GFP-53BP1 fluorescence was lower in the bleached area indicating slower 53BP1 diffusion (FIG. 4c). The decrease in diffusion kinetics was dependent on a wild-type 53BP1 sequence, because the GFP-53BP1 Asp1521Arg mutant protein diffused with fast kinetics in cells exposed to hypotonic media (FIG. 4c). Thus, changes in chromatin structure are sufficient to recruit 53BP1 to chromatin.

Very little is known regarding how cells sense the presence of DNA DSBs to activate DNA damage checkpoint pathways. It had been proposed that the tandem tudor domain of 53BP1 binds DNA directly[7]. However, the highly purified protein that we used for crystallization did not bind DNA (data not shown). It had also been suggested that 53BP1 is recruited to sites of DNA DSBs by binding to phosphorylated histone H2AX (γ-H2AX; ref. 6). Indeed, a region of 53BP1 that is N-terminal to the tandem tudor domain binds γ-H2AX in vitro (ref. 6) and retention of 53BP1 at sites of DNA DSBs requires histone H2AX (ref. 26). However, the initial recruitment of 53BP1 to sites of DNA DSBs is not defective in H2AX−/− cells[26] and the tandem tudor domain, which is sufficient for targeting 53BP1 to sites of DNA DSBs, does not bind γ-H2AX in vitro[6].

Figure 5:
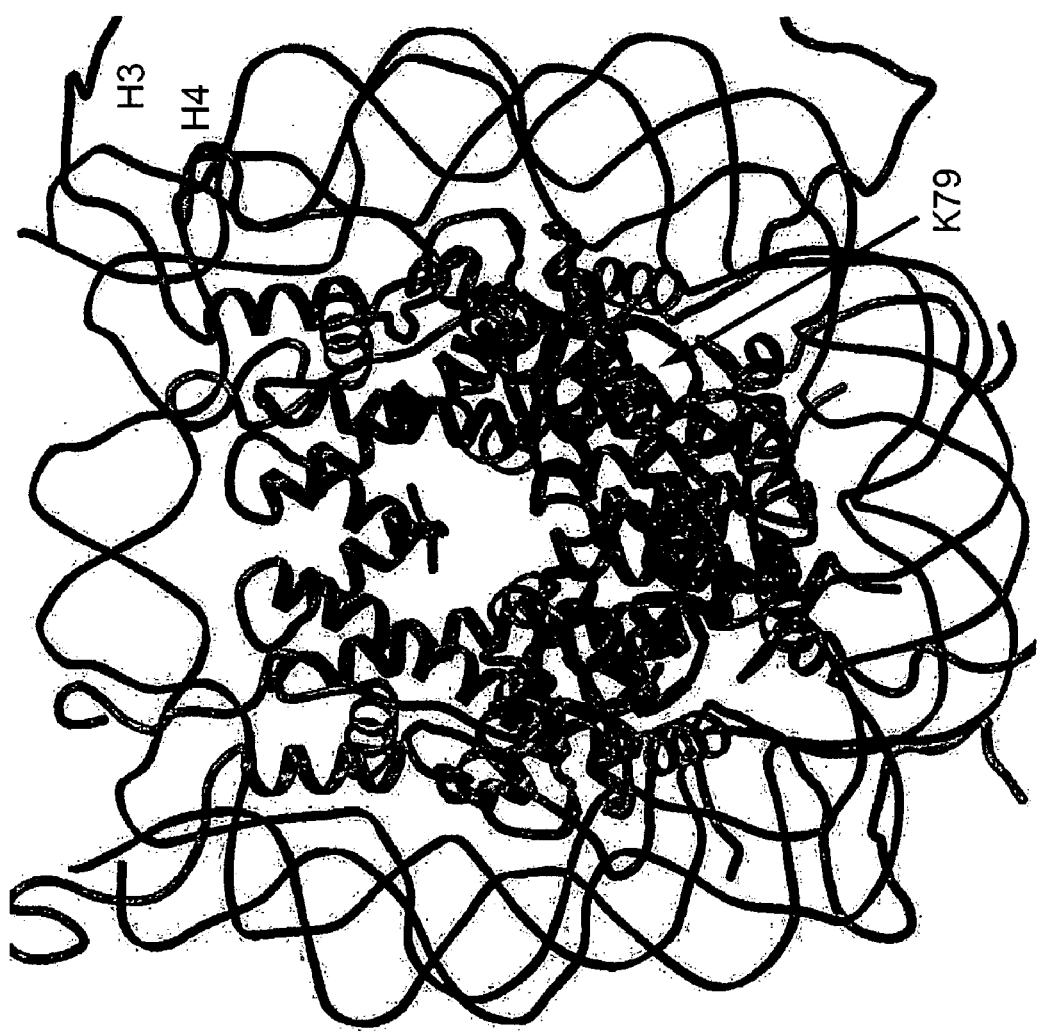
FIG. 5 Ribbons representation of the nucleosome structure showing the side chain of Lys79 (K79) of histone H3. The DNA backbone is colored blue; the histones are colored yellow, except for one histone H3 and one histone H4 molecule, which are colored pink and green, respectively.

The present studies indicate that 53BP1 targeting to sites of DNA DSBs is mediated by interaction of its tandem tudor domain with methylated Lys79 of histone H3. Lys79 of histone H3 is constitutively methylated in both mammalian and yeast cells[19-21] and at least in human cells irradiation did not lead to increased histone H3 Lys79 methylation. Therefore, DNA DSBs are likely to affect the accessibility of methylated Lys79 of histone H3 to 53BP1, possibly through changes in higher order chromatin structure[25]. Lys79 of histone H3 maps to the histone core (FIG. 5; ref. 27) and would be inaccessible to 53BP1, if higher order chromatin structure involves nucleosome stacking, as recently proposed[28]. Disruption of nucleosome stacking by DNA DSBs would lead to exposure of methylated Lys79 of histone H3, as well as of any other methylated residues in the histone core (T. Kouzarides, personal communication), resulting in recognition of the DSB by 53BP1 (FIG. 4d).

Methods

Structure Determination

A polypeptide corresponding to residues 1483-1624 of human 53BP1 was expressed in *E. coli* and purified by anion exchange (Sepharose Q and then Resource Q columns; Pharmacia) and gel filtration (Superdex 200 column; Pharmacia) chromatography. The protein (50 mg/ml) in buffer containing 25 mM BTP [pH 6.8], 200 mM KCl and 5 mM DTT was mixed with an equal volume of reservoir solution containing 18-21% PEG 3350 and 200 mM magnesium nitrate [pH 5.8] and crystals containing 10 molecules per unit cell were grown at 4° C. by the hanging drop vapor diffusion method.

Heavy atom derivatives were obtained by soaking the crystals in reservoir solution supplemented with 1.25 mM thimerosal and 5%-25% glycerol. Data collection and determination of the structure (Table 2) were performed as previously described[29]. Structure coordinates have been deposited in the Protein Data Bank under the accession code 1xni, which is hereby incorporated by reference in its entirety.

TABLE 2

Data Collection and Refinement Statistics.

| Unit Cell | | |
|---|---|---|
| Space Group | $P2_12_12_1$ | |
| Cell Dimensions (Å) | 71.610 × 157.664 × 179.723 | |
| Data Set | Native | Thimerosal |
| Resolution (Å) | 2.8 | 3.9 |
| Observations | 1,105,331 | 347,645 |
| Unique reflections | 51,072 | 19,161 |
| Data coverage (%) | 99.6 | 99.6 |
| Rsym (%) | 9.9 | 17.1 |
| Phasing analysis (20.0-2.8 Å) | | |
| Phasing power (centric) | — | 1.22 |
| Phasing power (acentric) | — | 1.41 |
| Rcullis (centric) | — | 0.76 |
| Rcullis (acentric) | — | 0.79 |
| Refinement statistics | | |
| Resolution range (Å) | 20.0-2.8 | |
| Reflections used (>0 sigF) | 48,979 | |
| Protein atoms | 9,480 | |
| Water molecules | 0 | |
| R-factor (%) | 24.7 | |
| Rfree (%) | 26.9 | |
| R.m.s. deviations | | |
| Bonds (Å) | 0.009 | |
| Angles (°) | 1.61 | |

TABLE 2-continued

Data Collection and Refinement Statistics.

| | |
|---|---|
| Ramachandran plot | |
| Most favored (%) | 89.0 |
| Allowed (%) | 11.0 |

$R_{sym} = \Sigma_h \Sigma_i |I_{h,i} I_h|/\Sigma_h \Sigma_i I_{h,i}$ for the intensity (I) of i observations of reflection h.
Phasing Power = $<F_{\lambda,i}>/E$, where $<F_{\lambda,i}>$ is the root-mean-square heavy atom structure factor and E is the residual lack of closure error.
$R_{cullis}$ = mean residual lack of closure error divided by the dispersive difference.
R factor = $\Sigma |F_{obs} - F_{calc}|/\Sigma |F_{obs}|$, where $F_{obs}$ and $F_{calc}$ are the observed and calculated structure factors, respectively.
$R_{free}$ = R factor calculated using 5% of the reflection data chosen randomly and omitted from the start of refinement.
Rms deviations for bonds and angles are the respective root-mean-square deviations from ideal values.

Intracellular Localization of GFP-53BP1 Fusion Proteins

U2OS osteosarcoma cells transiently expressing GFP fused to residues 1220-1711, 1480-1711 or 1-1972 of wild-type or mutant human 53BP1 were exposed to 3 Gy IR and examined 15 min later live by fluorescence microscopy. To study diffusion kinetics, cells expressing GFP fused to residues 1220-1711 of 53BP1 were cultured in regular media (DMEM supplemented with 10% fetal calf serum) or were switched 1 h before bleaching to hypotonic media (PBS with 100 mM NaCl supplemented with 0.45% glucose (w/v) and 1% serum). Part of a cell was bleached for 5 or 10 min using the mercury lamp of the microscope (100 W, Leica) and by partially closing its field diaphragm. During the recovery phase the cell was not illuminated. While on the microscope the cells were maintained at 37° C. using stage and objective lens heaters (Bioptechs). The results shown are representative of three independent experiments with at least three cells examined per experiment.

Histone H3 Binding

Glutathione S-transferase (GST) proteins (5 μg) fused to residues 1157-1634 or 1480-1626 of human 53BP1 or 750-917 of S. cerevisiae Rad9 were bound to glutathione beads (Pharmacia). The beads were then incubated for 1 h at 4° C. with histones in buffer containing 25 mM BTP [pH 6.8], 1 M KCl, and 0.5% Triton X-100. After 6 washes the bound material was resolved on SDS-polyacrylamide gels and either stained with Coomassie Brilliant Blue or immunoblotted with an antibody that recognizes the C-terminus of histone H3 (AbCam). The histones for these studies were derived from calf thymus (50 μg, Worthington), 293T cells (40 μg) or were expressed in E. coli (5 μg each of histone H3 and H4, Upstate). Histones from 293T cells were prepared by lysis in buffer containing 50 mM Tris-HCl [pH 8.0], 120 mM NaCl, 0.5% NP40, 1 mM DTT and protease-kinase-phosphatase inhibitors[1,5] for 45 min at 4° C. After centrifugation the pellet was incubated in buffer containing 10 mM HEPES, 1.5 mM MgCl$_2$, 10 mM KCl, 0.5 mM DTT, 1.5 mM PMSF and 0.25 N HCl for 1 h at 4° C. and the extracted histones were neutralized by adding one fifth volume 1.5 M Tris-HCl [pH 8.8]. For tandem mass spectrometry analysis, protein tryptic peptides were resolved on a reverse-phase liquid chromatography column, which was directly coupled to a quadrapole ion trap mass spectrometer, and the data were interpreted with SEQUEST software. Binding of GST-53BP1 to histones in the presence of competitor peptides (AbCam) was performed in buffer containing 25 mM BTP [pH 6.8], 250 mM KCl and 0.5% Triton X-100 for 1 h at 4° C.

Crosslinking

Proteins were crosslinked with formaldehyde[30]. Parental U2OS cells and U2OS cells expressing N-terminally His-tagged GFP-53BP1 fusion proteins containing residues 1220-1711 of 53BP1 were exposed to 9 Gy IR. 15 min later the cells were washed with PBS and incubated on ice for 20 min with Triton-X100 extraction buffer (10 mM PIPES [pH 6.8], 100 mM NaCl, 300 mM sucrose, 3 mM MgCl$_2$, 1 mM EGTA, 0.2% Triton X-100 and protease-kinase-phosphatase inhibitors). The cells were then rinsed with PBS, incubated for 10 min at 4° C. with 1% formaldehyde in PBS or just with PBS (mock-crosslinked) and then for 5 min with 0.1 M glycine. After a PBS wash, the cells were harvested by scraping and centrifuged. The pellet was incubated for 15 min on ice with lysis buffer (50 mM Tris-HCl [pH 7.5], 150 mM NaCl, 0.1% SDS and inhibitors), disrupted by sonication and diluted 10-fold in buffer containing 50 mM Tris-HCl [pH 7.5], 150 mM NaCl, 0.2% Triton X-100 and inhibitors. The disrupted pellet, hereafter referred to as Triton-X100 insoluble material, was incubated with Ni-NTA magnetic agarose beads (Qiagen) and bound proteins were eluted with imidazole. Histone H3 was detected by immunoblotting after the crosslinks were reversed by boiling.

Suppression of Histone H3 Methylation on Lys79

U2OS cells were transfected with control siRNA (luciferase; Dharmacon) or siRNA directed against human dot1L (GCUCGCUAUGGAGAAUUACdTdT), as previously described[5], except that for some cells the siRNA transfections were repeated every 4 days for a total of 3 rounds of transfections, because of the long half-life of histones and because histone methylation may not be reversible.

3 days after the last siRNA transfection, the cells were exposed to 9 Gy IR and 53BP1 intracellular localization was monitored by immunofluorescence 15 min later[5].

REFERENCES

1. Schultz, L. B., Chehab, N. H., Malikzay, A. & Halazonetis, T. D. p53 binding protein 1 (53BP1) is an early participant in the cellular response to DNA double-strand breaks. J. Cell Biol. 151, 1381-1390 (2000).
2. Xia, Z., Morales, J. C., Dunphy, W. G. & Carpenter, P. B. Negative cell cycle regulation and DNA damage-inducible phosphorylation of the BRCT protein 53BP1. J. Biol. Chem. 276, 2708-2718 (2001).
3. Anderson, L., Henderson, C. & Adachi, Y. Phosphorylation and rapid relocalization of 53BP1 to nuclear foci upon DNA damage. Mol. Cell. Biol. 21, 1719-1729 (2001).
4. Rappold, I., Iwabuchi, K., Date, T. & Chen, J. Tumor suppressor p53 binding protein 1 (53BP1) is involved in DNA damage-signaling pathways. J. Cell Biol. 153, 613-620 (2001).
5. Mochan, T. A., Venere, M., DiTullio, R. A., Jr. & Halazonetis, T. D. 53BP1 and NFBD1/MDC1-Nbs1 function in parallel interacting pathways activating ataxia-telangiectasia mutated (ATM) in response to DNA damage. Cancer Res. 63, 8586-8591 (2003).
6. Ward, I. M., Minn, K., Jorda, K. G. & Chen, J. Accumulation of checkpoint protein 53BP1 at DNA breaks involves its binding to phosphorylated histone H2AX. J. Biol. Chem. 278, 19579-19582 (2003).
7. Iwabuchi, K. et al. Potential role for 53BP1 in DNA end-joining repair through direct interaction with DNA. J. Biol. Chem. 278, 36487-36495 (2003).

8. Weinert, T. A. & Hartwell, L. H. The RAD9 gene controls the cell cycle response to DNA damage in *Saccharomyces cerevisiae*. *Science* 241, 317-322 (1988).
9. Willson, J., Wilson, S., Warr, N. & Watts, F. Z. Isolation and characterization of the *Schizosaccharomyces pombe* rhp9 gene: a gene required for the DNA damage checkpoint but not the replication checkpoint. *Nucleic Acids Res.* 25, 2138-2146 (1997).
10. Saka, Y., Esashi, F., Matsusaka, T., Mochida, S. & Yanagida, M. Damage and replication checkpoint control in fission yeast is ensured by interactions of Crb2, a protein with BRCT motif, with Cut5 and Chk1. *Genes Dev.* 11, 3387-3400 (1997).
11. Boulton, S. J. et al. Combined functional genomic maps of the *C. elegans* DNA damage response. *Science* 295, 127-131 (2002).
12. Charier, G. et al. The tudor tandem of 53BP1: a new structural motif involved in DNA and RG-rich peptide binding. *Structure (Camb.)* 12, 1551-1562 (2004).
13. Selenko, P. et al. SMN tudor domain structure and its interaction with the Sm proteins. *Nature Struct. Biol.* 8, 27-31 (2001).
14. Sprangers, R., Groves, M. R., Sinning, I. & Sattler, M. High-resolution X-ray and NMR structures of the SMN Tudor domain: conformational variation in the binding site for symmetrically dimethylated arginine residues. *J. Mol. Biol.* 327, 507-520 (2003).
15. Theobald, D. L., Mitton-Fry, R. M. & Wuttke, D. S. Nucleic acid recognition by OB-fold proteins. *Annu. Rev. Biophys. Biomol. Struct.* 32, 115-133 (2003).
16. Friesen, W. J., Massenet, S., Paushkin, S., Wyce, A. & Dreyfuss, G. SMN, the product of the spinal muscular atrophy gene, binds preferentially to dimethylarginine-containing protein targets. *Mol. Cell* 7, 1111-1117 (2001).
17. Brahms, H., Meheus, L., de Brabandere, V., Fischer, U. & Luhrmann, R. Symmetrical dimethylation of arginine residues in spliceosomal Sm protein B/B' and the Sm-like protein LSm4, and their interaction with the SMN protein. *RNA* 7, 1531-1542 (2001).
18. Kouzarides, T. Histone methylation in transcriptional control. *Curr. Opin. Genet. Dev.* 12, 198-209 (2002).
19. Feng, Q. et al. Methylation of H3-lysine 79 is mediated by a new family of HMTases without a SET domain. *Curr. Biol.* 12, 1052-1058 (2002).
20. van Leeuwen, F., Gafken, P. R. & Gottschling D E. Dot1p modulates silencing in yeast by methylation of the nucleosome core. *Cell* 109, 745-756 (2002).
21. Lacoste, N., Utley, R. T., Hunter, J. M., Poirier, G. G. & Cote, J. Disruptor of telomeric silencing-1 is a chromatin-specific histone H3 methyltransferase. *J. Biol. Chem.* 277, 30421-30424 (2002).
22. Game, J. C., Williamson, M. S. & Baccari, C. X-ray survival characteristics and genetic analysis for nine *Saccharomyces* deletion mutants that affect radiation sensitivity. *Genetics* doi:10.1534/genetics. 104.028613 (2004).
23. San-Segundo, P. A. & Roeder, G. S. Role for the silencing protein Dot1 in meiotic checkpoint control. *Mol. Biol. Cell* 11, 3601-3615 (2000).
24. Rogakou, E. P., Boon, C., Redon, C. & Bonner, W. M. Megabase chromatin domains involved in DNA double-strand breaks in vivo. *J. Cell Biol.* 146, 905-916 (1999).
25. Bakkenist, C. J. & Kastan, M. B. DNA damage activates ATM through intermolecular autophosphorylation and dimer dissociation. *Nature* 421, 499-506 (2003).
26. Celeste, A. et al. Histone H2AX phosphorylation is dispensable for the initial recognition of DNA breaks. *Nature Cell Biol.* 5, 675-679 (2003).
27. Luger, K., Mader, A. W., Richmond, R. K., Sargent, D. F. & Richmond, T. J. Crystal structure of the nucleosome core particle at 2.8 Angstrom resolution. *Nature* 389, 251-260 (1997).
28. Mozziconacci, J. & Victor, J. M. Nucleosome gaping supports a functional structure for the 30 nm chromatin fiber. *J. Struct. Biol.* 143, 72-76 (2003).
29. Hyen, Y. et al. Structural differences in the DNA binding domains of human p53 and its *C. elegans* ortholog Cep-1. *Structure (Camb.)* 12, 1237-1243 (2004).
30. Kannouche, P. L., Wing, J. & Lehmann, A. R. Interaction of human DNA polymerase eta with monoubiquitinated PCNA: a possible mechanism for the polymerase switch in response to DNA damage. *Mol. Cell* 14, 491-500 (2004).

The disclosures of each and every patent, patent application, publication, and accession number cited herein are hereby incorporated herein by reference in their entirety. The appended sequence listing is hereby incorporated herein by reference in its entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of identifying an agent that inhibits binding between 53BP1 (SEQ ID NO:1) or a H-3 binding fragment of 53BP1 comprising residues 1220 to 1771, 1480 to 1771, 1157 to 1634, 1480 to 1626, 1486 to 1602, 1483 to 1602, 1483 to 1624, or 1483 to 1606 of SEQ ID NO:1, and methylated Histone (H3) (SEQ ID NO: 2) capable of binding 53BP1 or a methylated 53BP1-binding fragment of histone H3 comprising residues 73-81 or 74-83, wherein said methylation corresponds to Lysine 79 of histone H3 comprising:
   a) contacting said 53BP1 or H3-binding fragment of 53BP1 and said H3 or 53BP1-binding fragment of histone H3 in the presence of a test agent; and
   b) determining whether the test agent inhibits binding between said 53BP1 or H3-binding fragment of 53BP1 and said H3 or 53BP1-binding fragment of histone H3 thereby identifying an agent which inhibits binding between 53BP1 and H3.

2. The method of claim 1, wherein step b) comprises comparing binding between said 53BP1 (SEQ ID NO. 1) or H3-binding fragment of 53BP1 and said H3 (SEQ ID NO. 2) or 53BP1-binding fragment of histone H3 in the presence of the agent and in the absence of the agent.

3. The method of claim 1, wherein the 53BP1 or H3-binding fragment of 53BP1 and methylated H3 or methylated 53BP1-binding fragment of histone H3 are exposed to the agent in a cell-free environment.

4. The method of claim 1, wherein the methylated H3 or methylated 53BP1-binding fragment of histone H3 is monomethylated, dimethylated, or trimethylated.

5. The method of claim 1, wherein the test agent is a small organic molecule, an antibody, siRNA, antisense oligonucleotide, peptide, or peptide mimetic.

6. The method of claim 1, wherein the 53BP1 or H3-binding fragment of 53BP1 and/or histone H3 or 53BP1-binding fragment of histone H3 are of isolated form.

7. The method of claim 1, wherein the 53BP1 or H3-binding fragment of 53BP1 or histone H3 or 53BP1-binding fragment of histone H3 further comprises a protein or peptide fused in frame.

* * * * *